United States Patent [19]

Lancashire et al.

[11] Patent Number: 5,786,186
[45] Date of Patent: Jul. 28, 1998

[54] DNA ENCODING ENZYMES OF THE GLYCOLYTIC PATHWAY FOR USE IN ALCOHOL PRODUCING YEAST

[75] Inventors: William Edward Lancashire, Bucks; John Richard Dickinson, South Glamorgan; Richard Anthony Malloch, Stirling, all of United Kingdom

[73] Assignees: Whitbread PLC, London; University College Cardiff Consultants Ltd., Cardiff, both of United Kingdom

[21] Appl. No.: 716,374

[22] PCT Filed: Mar. 22, 1995

[86] PCT No.: PCT/GB95/00648

§ 371 Date: Sep. 19, 1996

§ 102(e) Date: Sep. 19, 1996

[87] PCT Pub. No.: WO95/25799

PCT Pub. Date: Sep. 28, 1995

[30] Foreign Application Priority Data

Mar. 22, 1994 [GB] United Kingdom ............ 9405629

[51] Int. Cl.⁶ ............ C12N 1/19; C12N 15/52; C12N 15/63; C12P 7/06
[52] U.S. Cl. ............ 435/161; 435/254.2; 435/254.21; 435/320.1; 536/23.2
[58] Field of Search ............ 435/254.2, 254.21, 435/161; 536/23.2

[56] References Cited

FOREIGN PATENT DOCUMENTS

87/03006  5/1987  WIPO.
93/21333  10/1993  WIPO.

OTHER PUBLICATIONS

Temple et al., Bacteriol. 172:6396–6402, 1990.
Fraenkel, in *Escherichia coli* and *Salmonella typhimurium*: Cellular and Molecular Biology, Amer. Soc. Microbiol., Washington, DC, pp. 142–150, 1987.
*J. Bacteriol.* (1992) 174 (14), 4638–46.
*Mol. Microbiol.* (1991), 5(12), 2901–11.

*Primary Examiner*—Eric Grimes
*Attorney, Agent, or Firm*—Sughrue, Mion, Zinn, Macpeak & Seas, PLLC

[57] ABSTRACT

Yeast is transformed so that it is capable of expressing the enzymes phosphogluconate dehydratase and 2-keto-3-deoxygluconate 6-phosphate aldolase; whereby, in fermention, a sugar can be converted to pyruvate via the Entner-Doudoroff pathway. Recombinant DNA encodes the enzymes defined above, and includes one or more sequences which promote transcription and translation of the enzymes in yeast.

13 Claims, 12 Drawing Sheets

DNA ENCODING ENZYMES OF THE GLYCOLYTIC PATHWAY FOR USE IN ALCOHOL PRODUCING YEAST

FIELD OF THE INVENTION

This invention relates to recombinant DNA and to genetically-modified yeast for use in alcoholic fermentation.

BACKGROUND OF THE INVENTION

The familiar glycolytic pathway in *Saccharomyces cerevisiae*, in which sugars are converted into alcohol (the Embden-Meyerhof pathway; see Sequence A, below) has been studied intensively for many years because of its importance to the brewing, distilling, wine-making and baking industries, as well as for its inherent academic fascination. In the past, much effort has been devoted towards finding ways to get yeast to make more alcohol. This has taken two main directions: (1) the development of process monitoring and control procedures for product optimisation; and (2) strain selection and improvement programmes. Too often such ventures, having concentrated solely on the glycolytic pathway, have failed to take account of the physiological significance of the pathway to yeast.

Cuskey et al, J. Bacteriol. (June 1985) 162(3): 865–871, disclose the cloning of various genes specifying carbohydrate catabolism into strains of *Pseudomonas*. *P. aeruginosa* metabolises carbohydrates through the Entner-Doudoroff pathway (see Sequence B, below), and includes genes for glucose-6-phosphate dehydrogenase (ZWF), 6-phosphogluconate dehydratase (PGD) and 2-keto-3-deoxy-6-phosphogluconate aldolase (KGA); Cuskey et al produced a recombinant plasmid containing the genes for PGD and also glucokinase (GLK), but report that the structural genes for ZWF and KGA were not present on the cloned fragment.

Kawasaki et al, Biochem. Biophys. Res. Comm. (1982) 108(3):1107–1112, describe the cloning of various yeast glycolysis genes by complementation.

Banerjee et al, J. Gen. Microbiol. (1987) 133: 1099–1107, describe gluconeogenic mutations in *P. aeruginosa*, and recombinant plasmids carrying genes for fructose-bisphosphate aldolase (FBA), 3-phosphoglycerate kinase (PGK), NADP-linked glyceraldehyde-3-phosphate dehydrogenase (GAP) or KGA.

WO-A-8703006 describes yeasts having modified glycolysis rates, in order to increase the production of $CO_2$, ethanol and other fermentation products, and to decrease biomass production.

The sequences of the eda and edd genes (encoding PGD and KGA) in *E. coli* are reported by Egan et al, J. Bacteriol. 174:4638–4646 (1992). Corrections to these sequences are disclosed by Carter et al, Gene 130:155–6 (1993).

The production of fuel alcohol by bacterial systems, e.g. Xymomonas, is known. Such systems have a narrow substrate range and low alcohol tolerance.

An object behind the present invention is to modify yeast to enable more efficient conversion of sugars to ethanol, and consequently reduced energy benefit to the yeast cell.

SUMMARY OF THE INVENTION

According to a first aspect of the invention, yeast is genetically modified such that it is capable of expressing PGD (Enzyme Commission No. 4.2.1.12) and KGA (Enzyme Commission No. 4.1.2.14).

In addition to being able to express at least the enzymes given in Sequence A, and thereby convert a sugar to ethanol, unmodified yeast can express ZWF and phosphogluconate lactonase (PGL) which are the first two enzymes in Sequence B which are different from Sequence A. Accordingly, yeast of the invention provides a means whereby a sugar which is a conventional substrate for yeast-catalysed fermentation can be converted to pyruvate via Sequence B, i.e. the Entner-Doudoroff pathway.

According to a second aspect, novel recombinant DNA encodes PGD and KGA, and includes one or more sequences which promote transcription and translation of the enzymes in yeast.

DESCRIPTION OF THE INVENTION

The present invention is based on the observation that the production of ethanol is not the raison d'etre of a yeast cell. Ethanol is the waste product of an energy-yielding process that operates under conditions of low oxygen tension or high sugar concentration, enabling the yeast to grow and divide.

Energy yielded by yeast cultivation in the form of purine nucleoside triphosphates (such as ATP) is intended for cellular biosynthesis. In the context of the present invention, however, growth is not essential. To the brewing and distilling industry, and also for the production of, say, fuel alcohol, the production of biomass is merely a wasteful diversion of raw materials.

In Sequences A and B, * indicates a reaction in which 1 mol ATP is used; † indicates a reaction in which 1 mol ATP is generated, i.e. 2 mols per mol glucose in Sequence A. The net energy yield of Sequence A is 2 mol ATP. This is the energy normally used for biosynthesis. Sequence B generates ethanol more efficiently with reference to a given amount of starting material, since the net energy yield is only 1 mol ATP.

The illustrated Sequences show the conversion of glucose via glucose-6-phosphate. Glucose is of course merely an example of sugars which can be converted by unmodified yeast and by yeast modified in accordance with the invention.

In fermentation using genetically-unmodified *Saccharomyces cerevisiae*, more than 95% of glucose-6-phosphate is converted to fructose-6-phosphate via PGI; only a minor proportion is converted to 6-phosphoglucono-lactone via ZWF (and thence to 5-carbon sugars). It is not clear that yeast which has been genetically modified such that it expresses all the enzymes for Sequence B as well as for Sequence A will convert sugars such as glucose to ethanol via B rather than A; the use of materials or conditions that favour conversion via the Entner-Doudoroff pathway may be desirable.

One way in which conversion by Sequence B may be enhanced is by promoting translation of ZWF. It is preferred to interrupt Sequence A; in other words, yeast according to the invention preferably cannot express an enzyme among those by which glucose-6-phosphate is converted to pyruvate via the Embden-Meyerhof pathway. This is achieved most conveniently by deleting the appropriate gene sequence(s) from the yeast genome, or by introducing into the yeast a DNA sequence which transcribes an anti-sense message for the enzyme.

Preferably, the non-expressed enzyme is PFK. While all the other reactions of Sequence A are reversible (in gluconeogenesis) using the given enzymes, the conversion of fructose-1,6-bisphosphate to fructose-6-phosphate is catalysed by fructose bisphosphatase (FBP) rather than PFK.

Elimination of the gene(s) for PFK therefore inhibits glycolysis by the Embden-Meyerhof pathway, but does not inhibit gluconeogenesis.

Alternatively, the relevant enzyme may be chemically inhibited, in use. For example, PFK may be inhibited using ATP or citrate.

Sequence A yields (net) 2 mol NADH. Sequence B yields the same net amount of "reducing power", but in the form of 1 mol NADH and 1 mol NADPH (the latter arising in the conversion of glucose-6-phosphate to 6-phosphoglucono-lactone). Because NADH, and not NADPH, is the specific co-factor for ADH, yeast of the invention preferably additionally expresses an ADH which can utilise NADPH as a co-factor, e.g. a NADPH-specific ADH such as that found in *Thermoanaerobium brockii*. Such an enzyme may also exist in *Zymomonas spp* or, cryptically, in *S. cerevisiae*; if the latter, that would be the most desirable.

Yeast of the invention may be prepared by known modification/transformation techniques. Recombinant DNA for this purpose, which constitutes a further aspect of the invention, encodes or, if appropriate, includes a deletion for the relevant enzyme(s). Such DNA preferably includes promoter sequences which drive expression, but these may be unnecessary if naturally present in yeast. It may be constructed by known techniques. It is preferably derived from material in the animal, e.g. human or livestock, food chain.

DNA of the invention may comprise, for example, nucleotides containing transcriptional and translational information for both PGD and KGA, as well as selectable markers, located on a plasmid which can be inserted into yeast. Preferably, in order not to include unnecessary/unwanted DNA in the genome, it is preferred to integrate into the yeast genome the desired sequences; this can be done by known procedures, e.g. as described in EP-A-0231608.

Transformed yeast of this invention may be used to produce commercial spirit more efficiently, or in fuel alcohol production. Advantages of this invention over known fuel alcohol production systems are a much wider substrate range, and increased alcohol tolerance.

Transformed yeast of the invention may be used to ferment alcoholic beverages such as beer, cider and wine. It may also be used in the fermentation stages of potable spirits such as gin and vodka. For any of these purposes, the yeast may preferably be provided in immobilised form. A conventional support, and a conventional immobilisation technique, may be used.

Yeast of the invention has high alcohol tolerance, e.g. up to 15%, or more. It thus facilitates use and also shipping, e.g. by reducing the amount of water involved.

The novel yeast or DNA may include a switchable/conditional expression system, e.g. a controllable promoter of known type, such that either or each pathway may be switched on or off by selection of reagents or conditions. For example, a controllable promoter of known type may be used, e.g. an unnatural promoter that is responsive to heat. The presence of such a system makes it possible to switch off the yeast's utilisation of Sequence B during culture, and of Sequence A during fermentation.

| Sequence A | Sequence B |
|---|---|
| Glucose | Glucose |
| *↓ HXK,GLK | ↓ HXK,GLK |
| Glucose-6-P | Glucose-6-P |

-continued

| Sequence A | | Sequence B |
|---|---|---|
| ↓ PGI | | ↓ ZWF |
| Fructose-6-P | | 6-P-Gluconolactone |
| *↓ PFK | | ↓ PGL |
| Fructose-1,6-P2 | | 6-P-Gluconate |
| ↓ FBA,TPI | KGA | ↓ PGD |
| Glyceraldehyde-3-P | ← | 2-Keto-3-deoxy-6-P-gluconate |
| ↓ GLD | | |
| 1,3-Diphosphoglycerate | | |
| ↑↓ PGK | | |
| 3-P-Glycerate | | |
| ↓ GPM | | ↓ KGA |
| 2-P-Glycerate | | |
| ↓ ENO | | |
| Phosphoenolpyruvate | | |
| ↑↓ PYK | | |
| Pyruvate | | Pyruvate |
| ↓ PDC | | ↓ PDC |
| Acetaldehyde | | Acetaldehyde |
| ↓ ADH | | ↓ ADH |
| Ethanol | | Ethanol |

The following Examples illustrate the invention, in connection with the References and also the accompanying drawings, in which.

Figure 6:
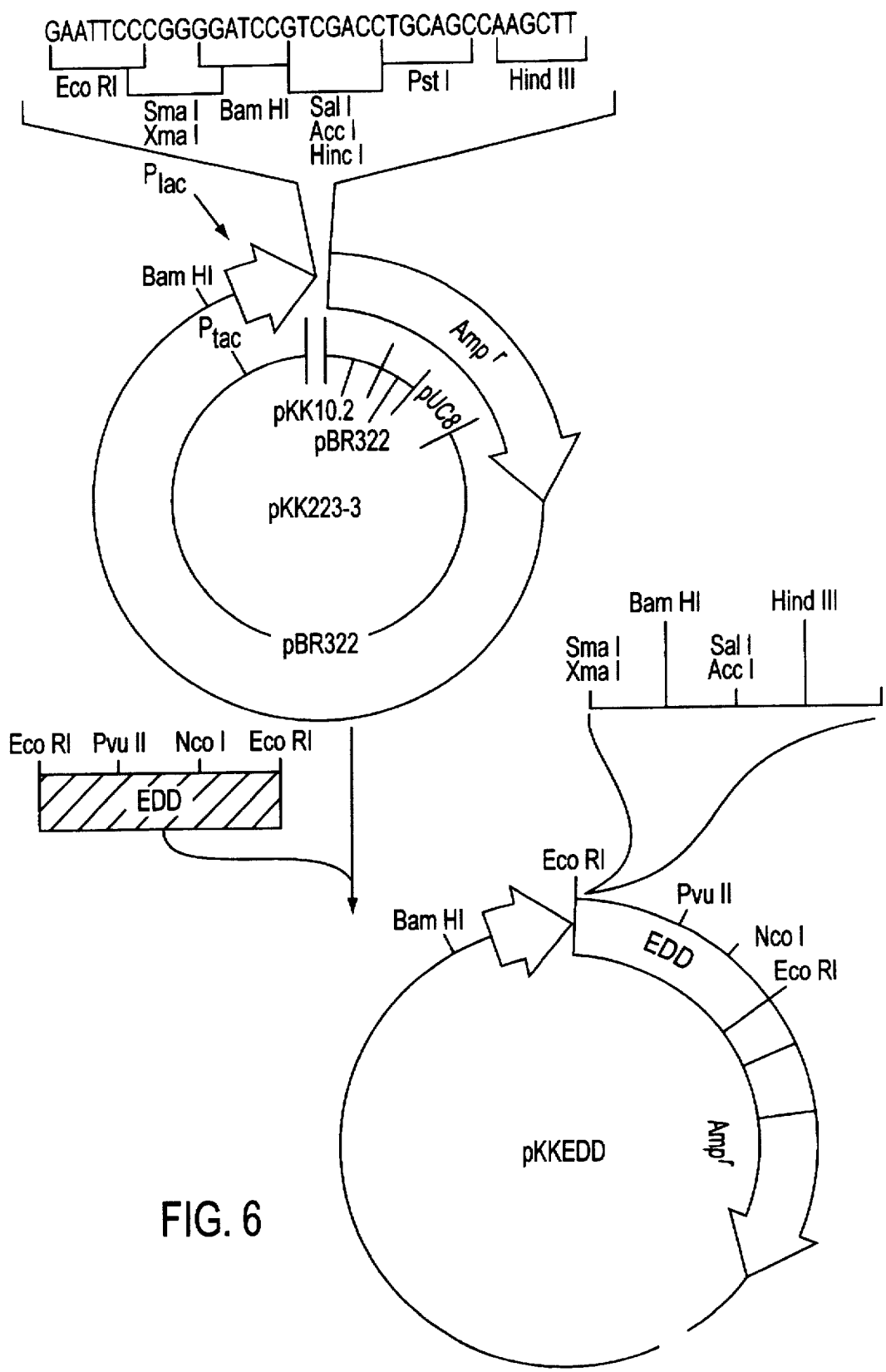
Figure 7:
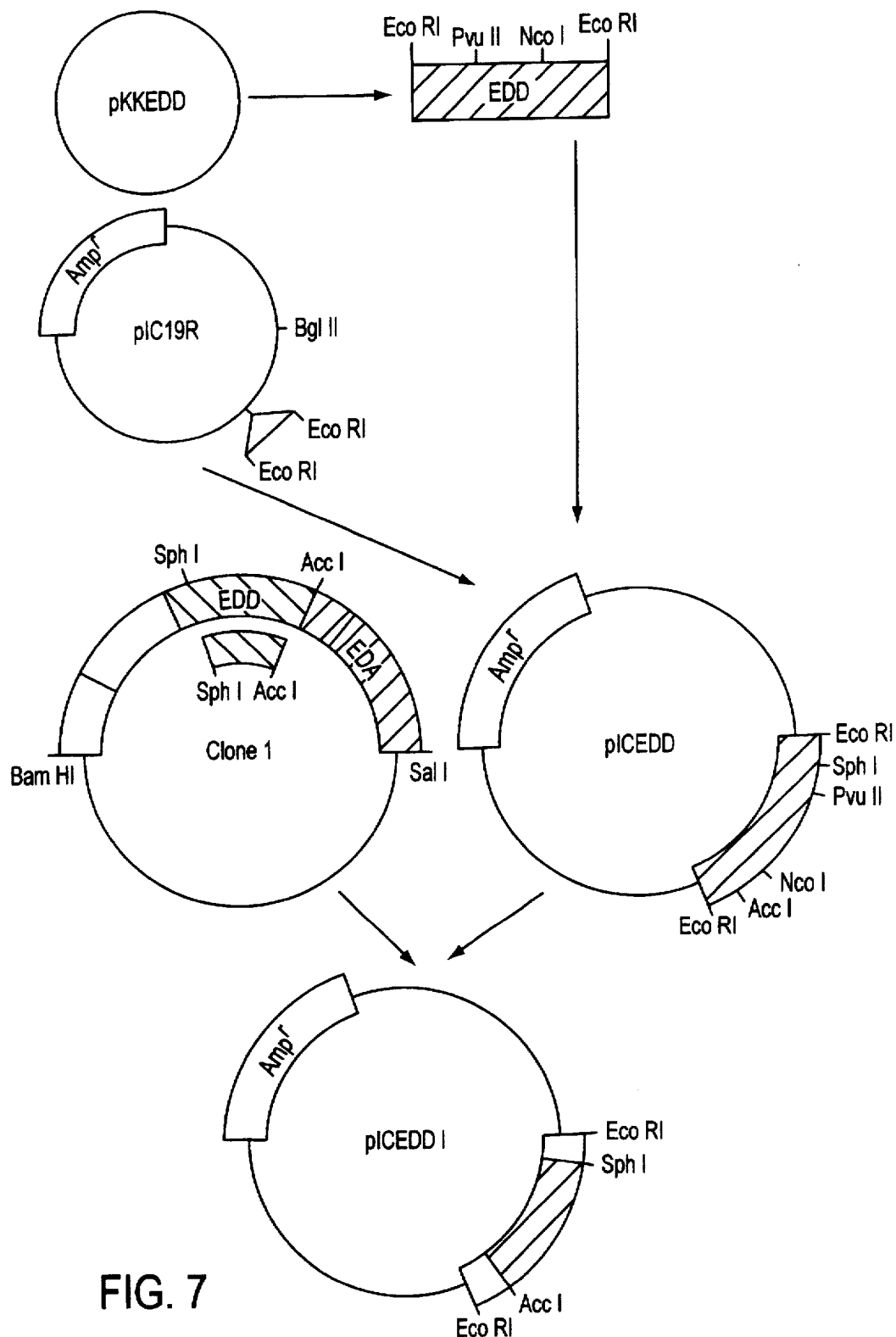

FIG. 6 schematically represents the steps involved in the construction of a vector containing the non-functional PCR-amplified edd DNA FIG. 7 shows the scheme used to replace the PCR-induced errors in the edd DNA.

Figure 8:
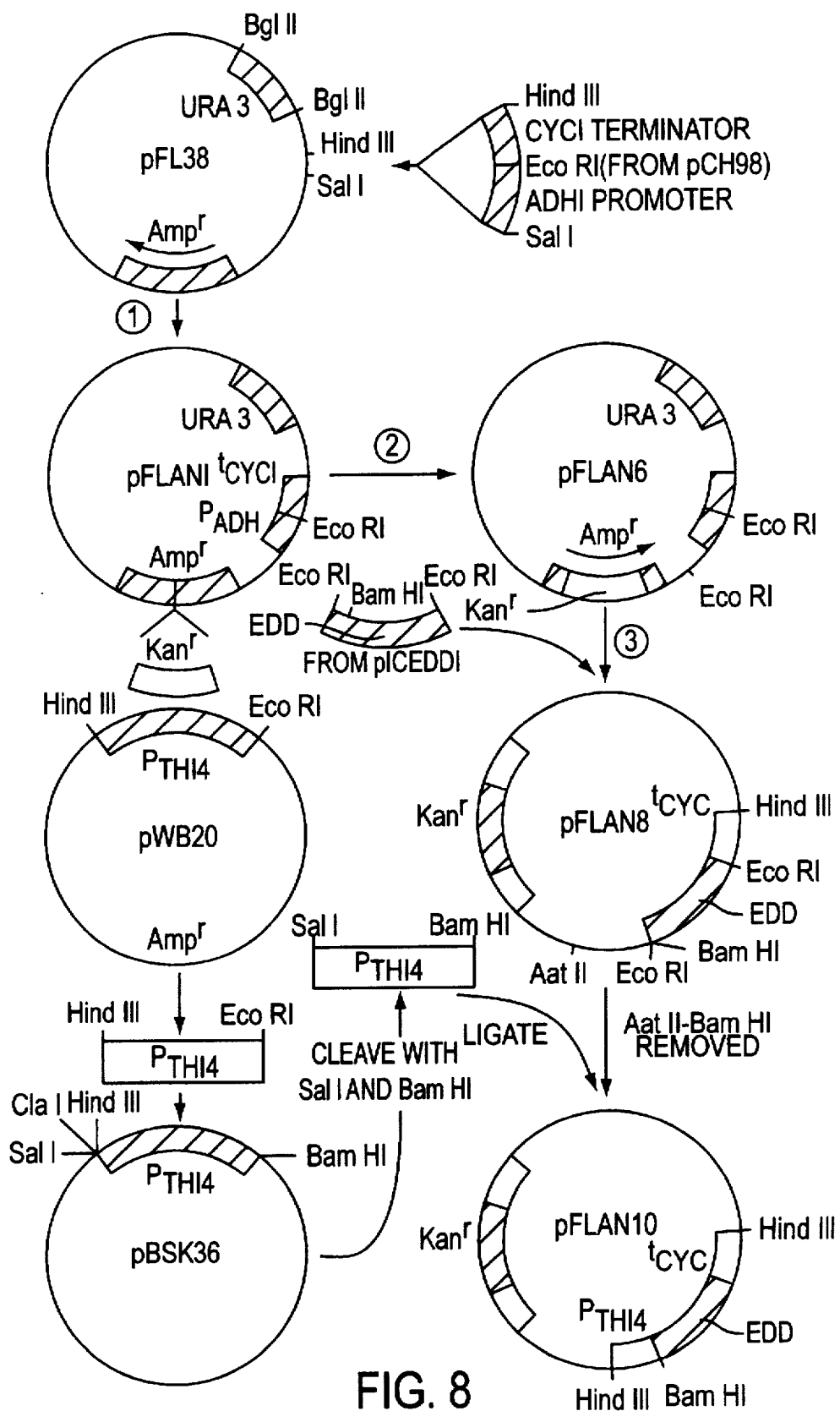

FIG. 8 represents the construction of an edd yeast expression vector.

Figure 9:
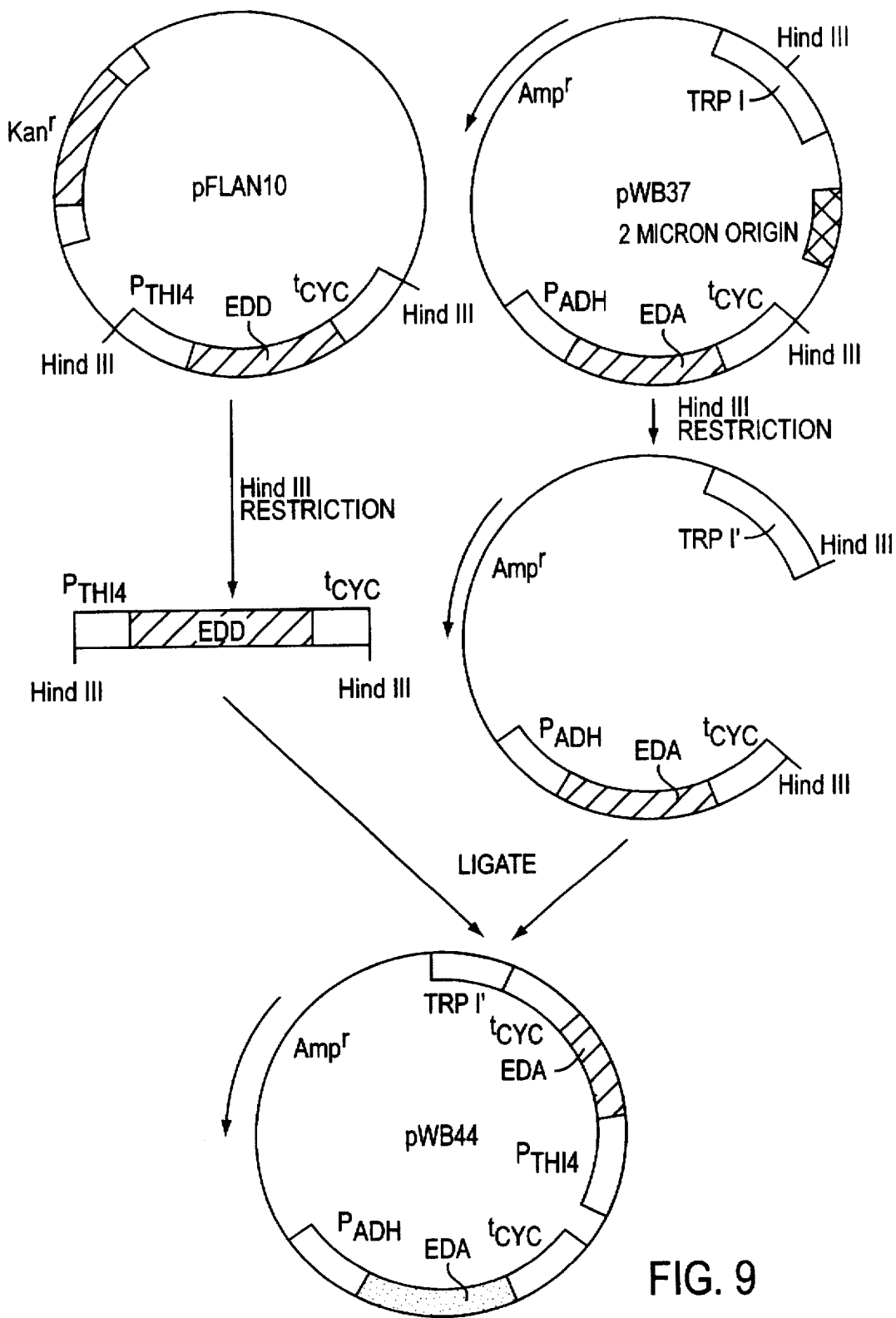

FIG. 9 shows the construction of the yeast edd/eda integration vector.

Figure 10:
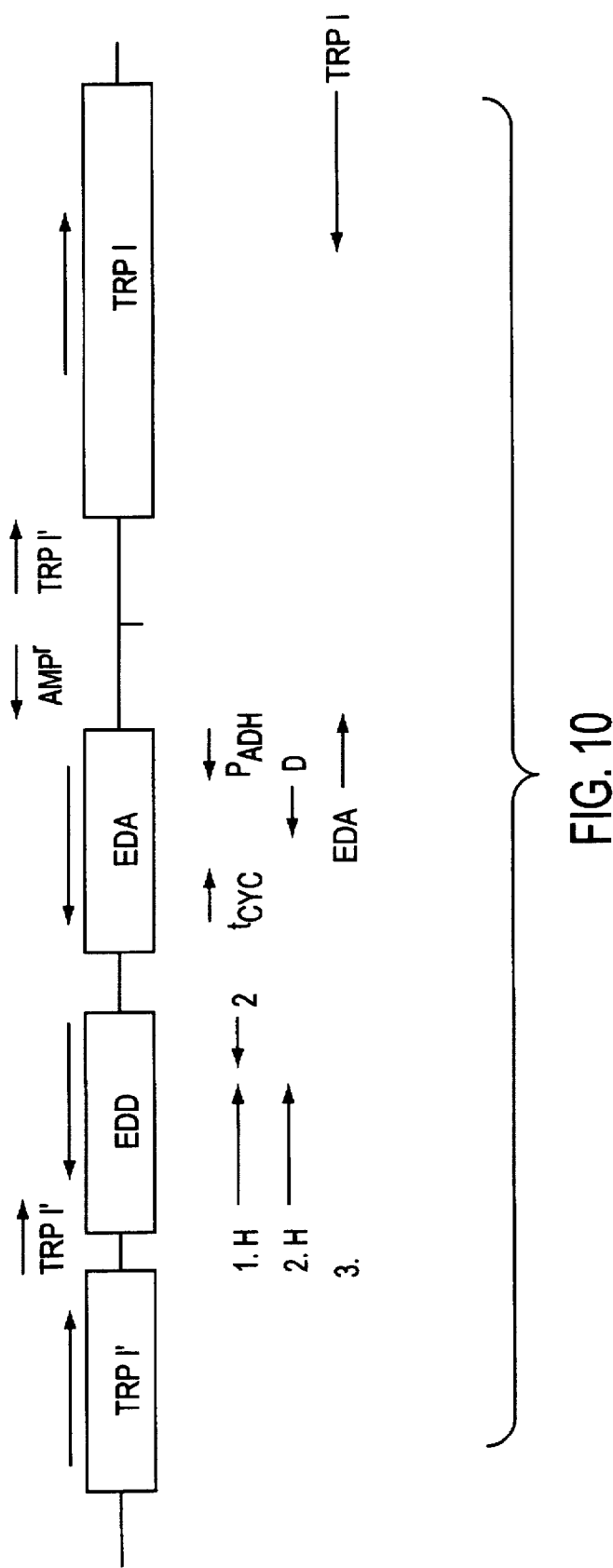

FIG. 10 shows the PCR strategy for verification of transformed construction (verification of (1) presence of EDA and EDD in 37.1.6 transformants; (2) position and orientation of genes; (3) site of integration of pWB44).

Figure 11:
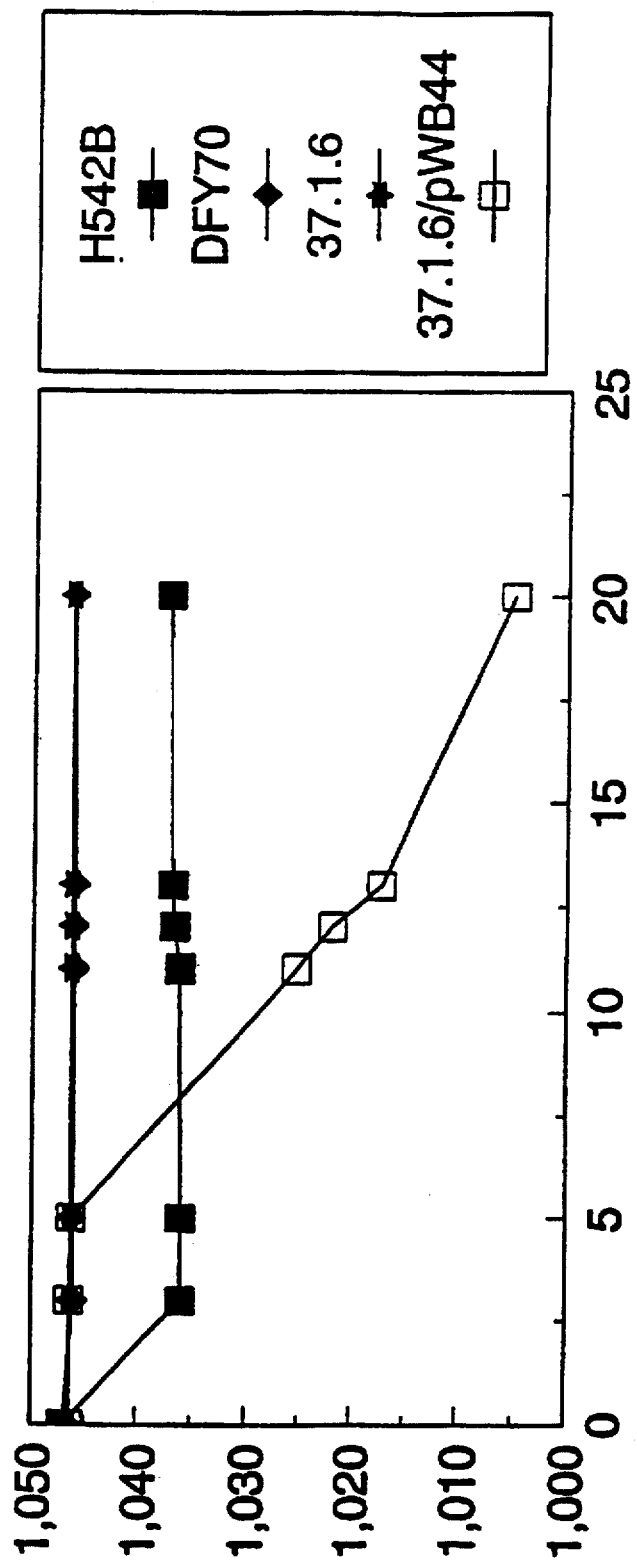
Figure 12:
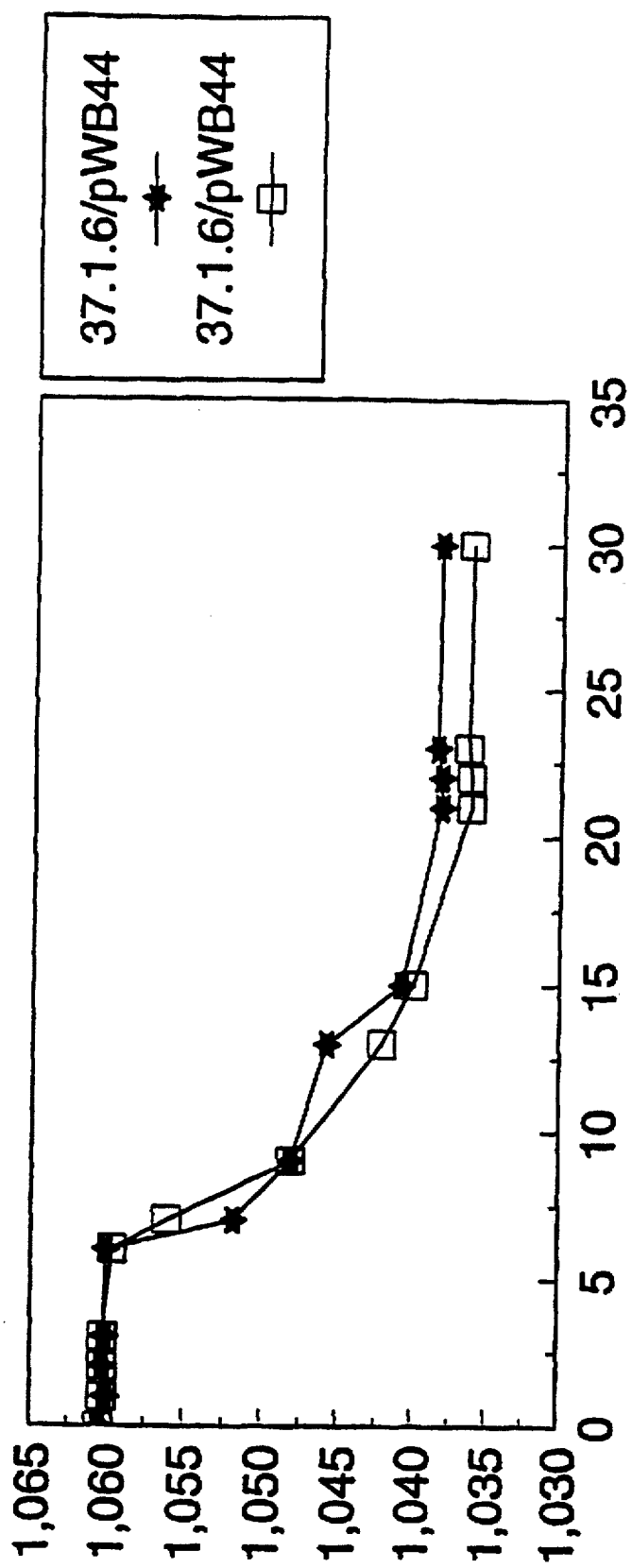

FIGS. 11 and 12 show fermentation profiles of Present Gravity against Time (days) of yeasts in minimal synthetic growth medium and brewer's wort media respectively.

EXAMPLES

Sub-cloning of plasmid pLC37-44 (Clarke & Carbon 1976)

Figure 1:
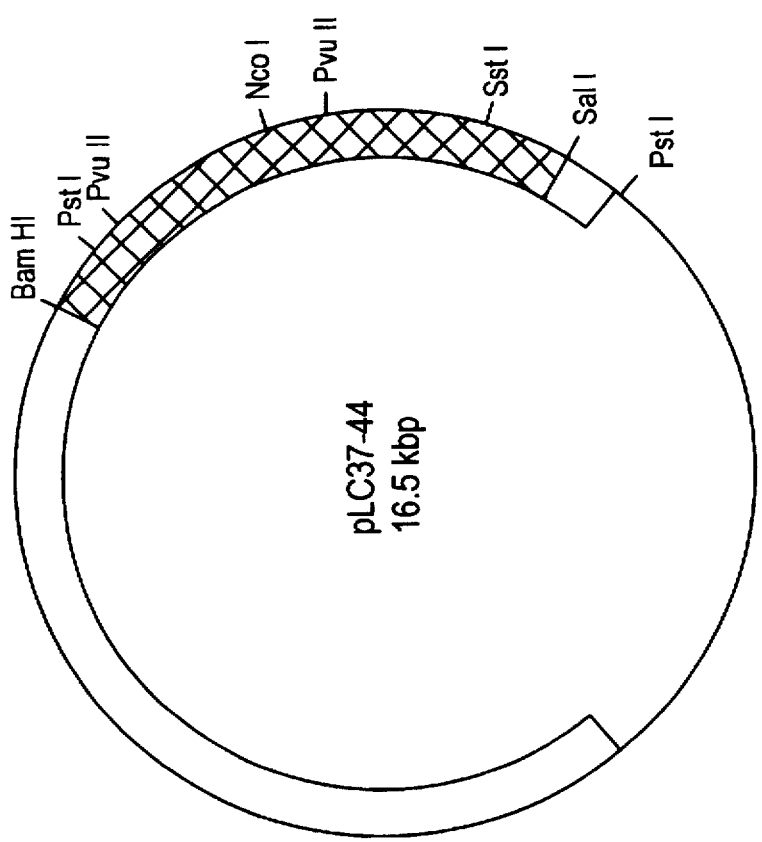
FIG. 1 represents the plasmid pCL37-44 isolated from the *E. coli* gene library constructed by Clarke and Carbon (1976), which contains the edd and eda genes.

Plasmid pLC37-44 is a clone from the *E. coli* gene library (Thomson et al 1979) isolated in *E. coli* strain JA200 and known to contain the genes eda and edd of the Entner-Doudoroff pathway (Clarke & Carbon 1976). Genes eda and edd code respectively for the enzymes 2-keto-3-deoxy-6-phosphogluconate aldolase (KGA) and 6-phosphogluconate dehydratase (PGD). The physical map of pLC37-44 was generated by restriction endonuclease cleavage analysis and is shown in FIG. 1. Sub-clones were obtained using conventional recombinant DNA methods and publicly available materials. All restriction enzymes were purchased from IBI or Gibco BRL unless otherwise stated. T4 polymerase and T4 DNA ligase were obtained from Pharmacia.

Figure 2:
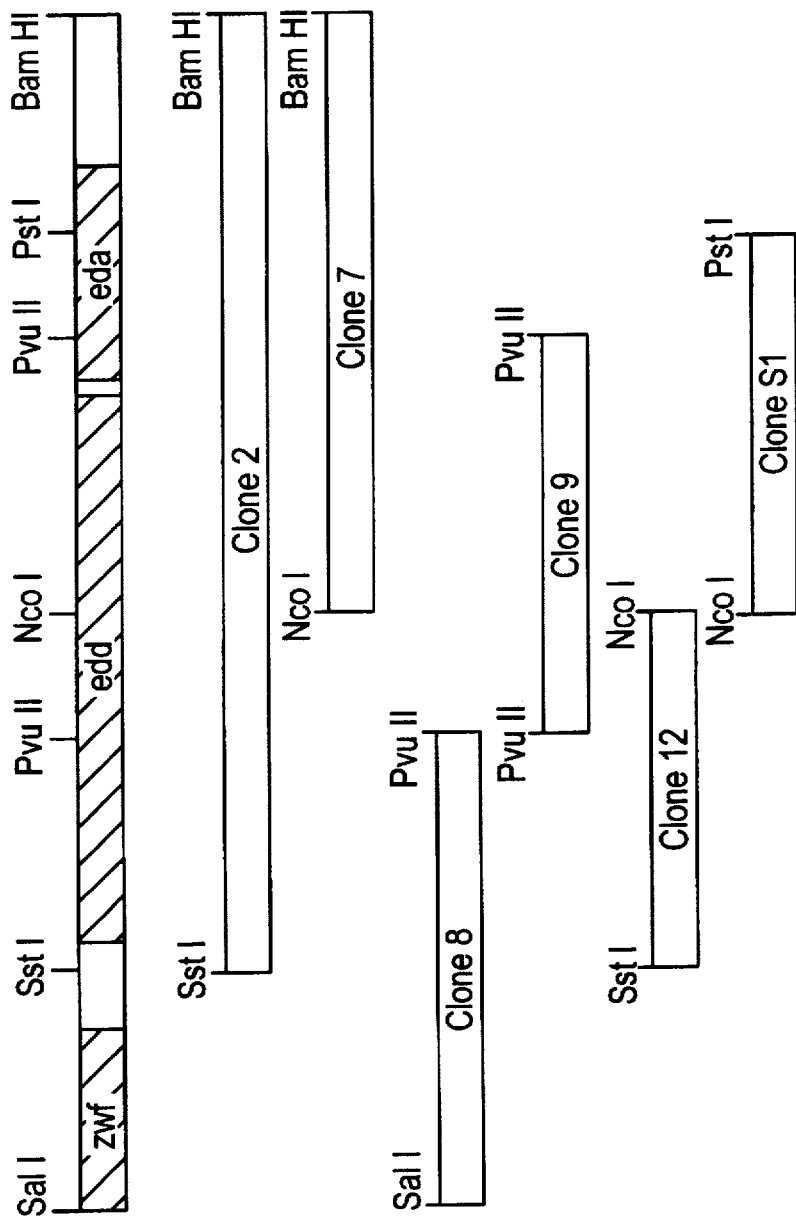
FIG. 2 shows the physical map of the zwf, edd, eda locus (see also Egan et al and Carter et al, supra), and the sequencing primers employed to determine the nucleotide sequence of the three open reading frames. Also represented are the inserts cloned into the vector PGEM 7 zf(+).
Figure 3:
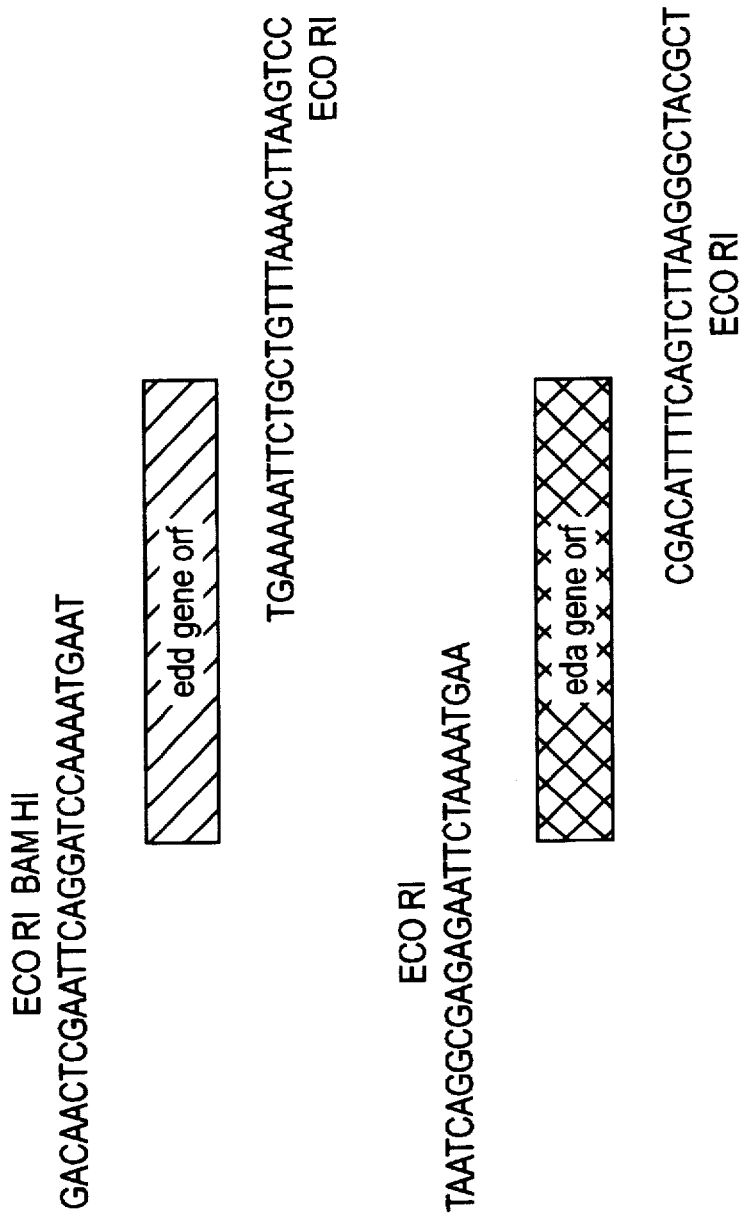
FIG. 3 represents the edd and eda open reading frames and the binding positions of the synthetic oligonucleotides used in amplification of the two genes.

Smaller fragments (see FIG. 2; cf also Egan et al and Carter et al, supra) were sub-cloned into pGEM7 zf(+) obtained from Promega. The sub-clones were maintained in *E. coli* strain JM109 (Yanisch-Perron et al 1985).

Preparation of cell extracts

*E. coli* strains were grown at 37° C. in minimal media containing 20 mM glucose or sodium gluconate. The composition of the standard minimal medium was (g/l in distilled $H_2O$); $KH_2PO_4$.5; $(NH_4)_2SO_4$ adjusted to pH 7.2, 1; $MgSO_4 \cdot 7H_2O$, 0.05; $FeSO_4 \cdot 7H_2O$, 0.005. The magnesium and iron salts were sterilised separately as a solution of 5% (w/v) $MgSO_4 \cdot H_2O$ and 0.5% (w/v) $FeSO_4 \cdot 7H_2O$); these were added aseptically in the correct proportions to the other already sterilised constituents.

After 1% inoculum and 18 hours of growth incubation, 300 ml culture was harvested by centrifugation at 7000 rev/minute for 15 minutes in a Sigma 4K10 centrifuge. Harvested cells were washed twice in 15 mM phosphate buffer, resuspended in 20 ml 20 mM phosphate buffer (pH 7.8) containing 1 mM DTT (dithiothreitol) and stored on ice.

A MSE Soniprep 150 ultrasonic disintegrator with a titanium probe (tip diameter 9.5 mm) operating at 20 μm was used to sonicate 20 ml washed cell suspension for a total exposure time of 1.67 minutes. The vessel containing the cell suspension was surrounded by ice and sea salt. Sonication was applied in short bursts of 20 seconds with 99 second intervals for cooling. During the second and fourth interval the cooling process was monitored with a thermometer and the subsequent sonication bursts were not applied until the temperature of the cell suspension had fallen below 4° C.

The disrupted cells were centrifuged at 100,000 g for 90 min at 4° C. using a Beckman L8-70M Ultracentrifuge. The supernatant was decanted and stored on ice.

Enzyme assays were carried out as described by Narbad et al 1988. Reactions were conducted in 1 ml cuvettes using Kontron Uvikon 860 spectrophotometer.

The results in Table 1 indicate that, in the strains without the cloned fragments, the enzymes of the ED pathway were induced only during growth on gluconate and the expression of chromosomally-encoded enzymes was repressed during growth on glucose. In JM109 cells transformed with either Clone 1 or Clone 2 plasmid high levels of ED pathway enzymes were detected during growth on glucose indicating a constitutive expression of plasmid encoded enzyme.

Amplification of the eda open reading frame

Two oligo-nucleotides were synthesised using an Applied Biosystems (ABI381A) DNA synthesiser. Alterations were made from the native chromosomal sequence to incorporate EcoRI restriction endonuclease cleavage sites and to alter the codon upstream from the eda initiation codon to AAA. This alteration is important when the eda gene is expressed in yeast.

native    5'TAATCAGGCGAGAGAAAACTCTGATGAA3'
synthetic 5'TAATCAGGCGAGAGAATTCT<u>AAA</u>ATGAA3'
                                 EcoRI native    5'TCGCATCGGGCATTTTGACTTTTACAGC3'
synthetic 5'TCGCATCGGGAATTCTGACTTTTACAG3'
                      EcoRI The eda gene was amplified using the following polymerase chain reaction (PCR) techniques: Purified Clone 2 DNA (FIG. 2) 50 ng, 0.4 ng of each of the synthetic oligonucleotides, 10 μl PCR reaction buffer 10x (Perkin-Elmer), 2 units of Taq polymerase (Perkin-Elmer) water up to 100 μl and mineral oil (60 μl) were mixed in a 0.5 ml microcentrifuge tube. Using a Perkin-Elmer thermal cycler the following cycle conditions were used: 1st cycle 90° C. for 2 minutes, 2nd cycle 92° C./2 minutes, 55° C./3 minutes, 82° C./2 minutes; followed by a further 28 cycles at: 90° C./2 minutes, 53° C./3 minutes, 72° C./2 minutes.

Analysis of the reaction mixture by flat-bed gel electrophoresis (Maniatis et al 1982 p.159) revealed a single band of 660 base pairs. Purification of the DNA from the gel was performed using an IBI electroelution unit using 3M sodium acetate as described in the manufacturer's operating instructions. The DNA was centrifuged at 13000 rpm at 4° C. in a MSE Microcentrifuge for 10 minutes. The supernatant was carefully removed and 500 μl of 70% v/v ethanol was added to the DNA. The sample was carefully mixed and the contents recentrifuged as previously. Following a second 70% v/v ethanol addition and centrifugation, the DNA was dried and resuspended in 6 μl of sterile water, 2 μl of 10x restriction buffer C (IBI) and 20 units of EcoRI restriction endonuclease (IBI). Incubated in a water bath at 37° C. for 3 hours. After 60 minutes 2 μl of 40 mM spermidine was added to the reaction mixture. The mixture was purified again using flat-bed gel electrophoresis and electroeluted as previously.

Construction of the eda bacterial expression vector

Figure 4:
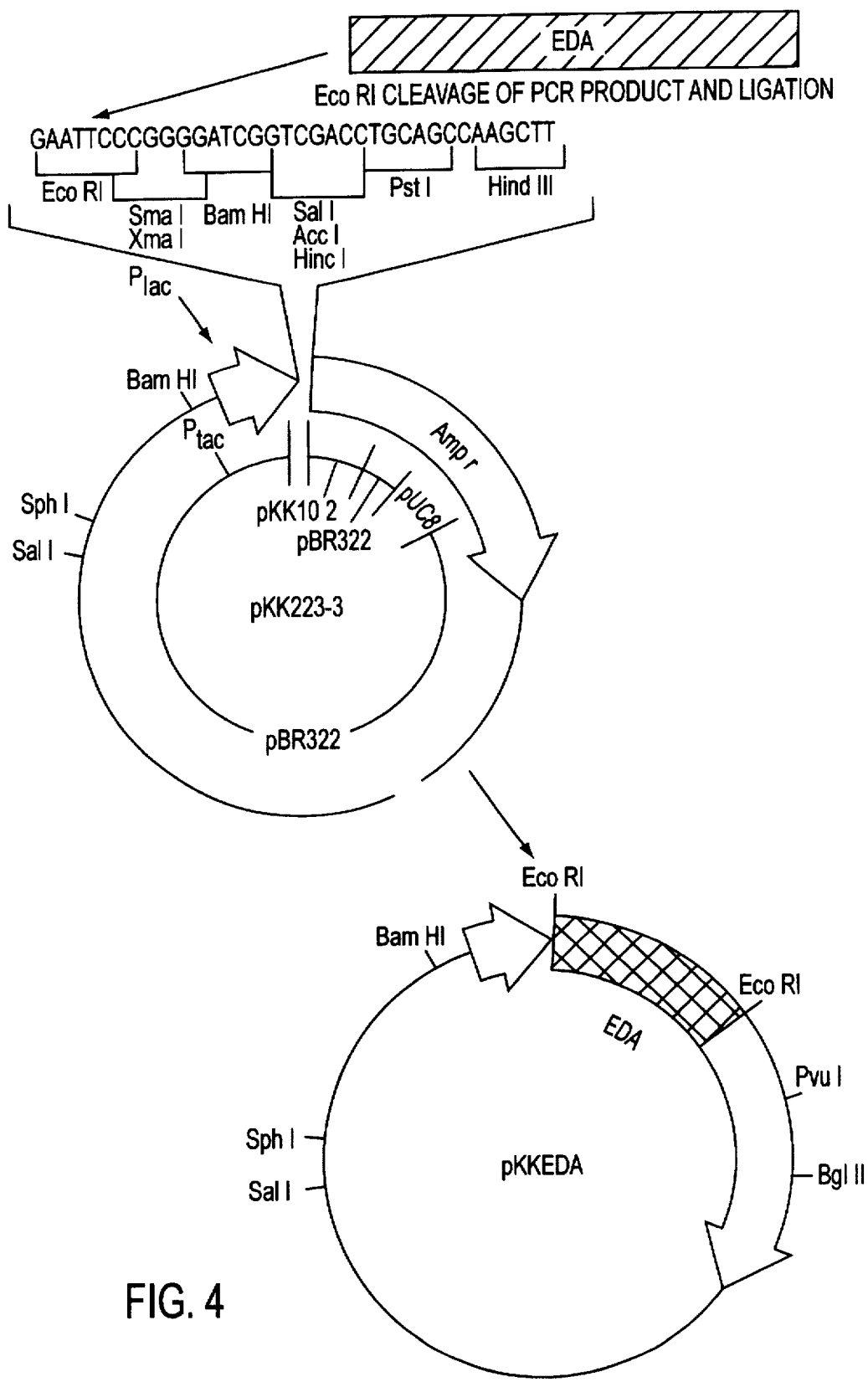
FIG. 4 is a schematic representation of the steps involved in the construction of an eda bacterial expression vector.

The eda bacterial expression vector pKKEDA was constructed by cloning the eda PCR amplified product into pKK223-3 (Pharmacia), as shown in FIG. 4.

The vector pKK223-3 (600 μg) was cleaved with EcoRI (20 units) in IBI in a total reaction volume of 20 μl with 2 μl of 10x reaction buffer C (IBI) added. The mixture was incubated at 37° C. for 3 hours but 2 μl of 40 mM spermidine was added after 60 minutes. The cleaved vector was gel purified using flat-bed agarose gel eletrophoresis (Maniatis et al. 1982 p. 159). The single band of 4585 base pairs was excised and electroeluted using an IBI electroelution unit. DNA retardation and precipitation was using 3M sodium acetate exactly as described in the manufacturer's instructions. The DNA was then washed in 70% v/v ethanol as described previously and resuspended in 6 μl of sterile distilled, deionised water.

Ligation of the DNA fragment containing the eda coding region into plasmid pKK223-3 was performed in the following reaction mix:

| | |
|---|---|
| eda PCR fragment | 1 μl (300 μg) |
| pKK223-3 EcoRI cleaved | 2 μl (200 μg) |
| 10 × ligation buffer (Pharmacia) | 1 μl |
| T4 DNA ligase (Pharmacia) | 0.5 μl |
| 10 mM ATP | 1 μl |
| Water | 4.5 μl |

The above reaction mixture was incubated at 10° C. for 16 hours. Following ligation the mixture was diluted to 100 μl with 5 µl 20×SSC (Maniatis et al 1982 p.396) and 95 µl of sterile distilled, deionised water.

Transformation of the ligation mix into *E. coli* strain JM105 was as described by Maniatis et al 1982 p.250. The transformation mixes were plated onto LB agar supplemented with 50 µg/ml ampicillin, 500 transformants were obtained after overnight incubation at 37° C. Colony hybridisation were performed on 100 of the transformants (Maniatis et al 1982 p.324).

Random-primed $\alpha^{32}$P-dCTP eda PCR-amplified product was used to probe the DNA from these transformants. Potentially positive eda clones were detected by their signal intensity compared with that of the transformants not possessing an eda insert in the pKK223-3 plasmid. Of the 100 transformants, 26 gave a positive reaction. Small-scale plasmid isolations were conducted on these 26 clones (Maniatis et al 1982 p. 250). To establish the orientation of the inserted DNA, the eda positive plasmids were cleaved with PvuI restriction endonuclease (10 units) in a total reaction volume of 20 µl containing 2 µl of 10x reaction buffer. The reactions were incubated for 3 hours at 37° C. prior to analysis by flat-bed agarose gel electrophoresis (Maniatis et al 1982 p. 159). Plasmid pKK23-3 containing an eda inserted into it, cleaved twice (FIG. 4). Plasmids containing the eda gene in the correct orientation were characterised by the presence of a 773 base pair fragment. The eda insert in the incorrect orientation is characterised by the presence of a 1025 base pair fragment. Five of the 26 transformants possessed the eda gene in the correct orientation. These correctly oriented plasmids were designated pKKEDA.

Verification of eda expression in *E.coli*

*E. coli* strain N3041 is defective in the eda gene product (Shurvinton et al 1984). The five correctly oriented eda containing pKK223-3 plasmids were transformed into the strain N3041 (Maniatis et al 1982 p. 250). Transformants were selected. The presence of pKK223-3 with eda cloned in the correct orientation (pKKEDA) in N3041 gave a wild-type phenotype, i.e. a functional eda gene product.

The eda gene resident in plasmid pKKEDA was sequenced. The nucleotide sequence determined, was exactly as found in the plasmid pLC37-44 except for: the alterations at the 5' and 3' ends due to the synthetic oligonucleotides used for the PCR amplification of the gene (see FIG. 2); and at position 2988 (Carter et al) where the codon, AAA, coding for lysine was altered to AAT, also coding for lysine. This conservative change made no alteration to the amino acid sequence of the eda protein (KGA).

Construction of the eda yeast expression vector

The yeast expression plasmid pCH100 (C. Hadfield et al 1987) and pKKEDA were cleaved with EcoRI as follows: 1 µg of plasmid DNA was cleaved with 20 units of EcoRI restriction endonuclease (IBI), 2 µl of 10x reaction buffer C in a total reaction volume of 20 µl. The mixture was incubated at 37° C. for 3 hours. 2 µl of 40 mM spermidine was added after 60 minutes incubation.

The digested plasmids were analysed by flat-bed agarose gel electrophoresis (Maniatis et al 1982 p. 159). The 660 base pair fragment from pKKEDA and the 7490 base pair fragment of pCH100 were excised from the gel. Both fragments were purified by the Geneclean II kit (BIO 101, CA, USA) exactly as described by the manufacturer's instructions.

Ligation of the eda gene fragment, and vector pCH100 was carried out in the following mixture.

| | |
|---|---|
| eda DNA | 3 µl (200 ng) |
| pCH100 DNA | 3 µl (100 ng) |
| 10 × ligase buffer (Pharmacia) | 1 µl |
| T4 DNA ligase (Pharmacia) | 1 µl |
| 10 mM ATP | 1 µl |
| Water | 1 µl |

The reaction mixture was incubated at 15° C. for 16 hours and then diluted to 50 µl with sterile water.

The *E. coli* strain JM109 (Yanisch-Perron et al 1985) was transformed with the above ligation reaction as described by Maniatis et al 1982 p. 250. Selection for transformants was carried out on LB agar supplemented with 50 µl/ml ampicillin. The plates were incubated at 37° C. for 24 hours. Three hundred transformants were restreaked onto duplicate LB agar plates supplemented with 50 µl/ml ampillicin. Colony hybridisations were performed on the transformants. $\alpha^{32}$P-dCTP random-primed purified eda DNA was used to probe the transformant DNA. As *E. coli* possesses a single chromosomally-located copy of the gene, intensity over background due to plasmid-borne multi-copies of the gene, was looked for. Twenty six transformants clearly showed an increase in intensity on the autoradiograph. Small-scale plasmid isolations were conducted on these 26 positive eda clones. Orientation of the eda fragment was determined by digestion of the 26 plasmids with the restriction endonucleases SphI and PstI (IBI) in the following mixture.

| | |
|---|---|
| Plasmid DNA | 8 µl (200 ng) |
| SphI | 1 µl (10 units) |
| PstI | 1 µl (10 units) |
| 10 × reaction buffer A (IBI) | 2 µl |
| Water | 8 µl |

Figure 5:
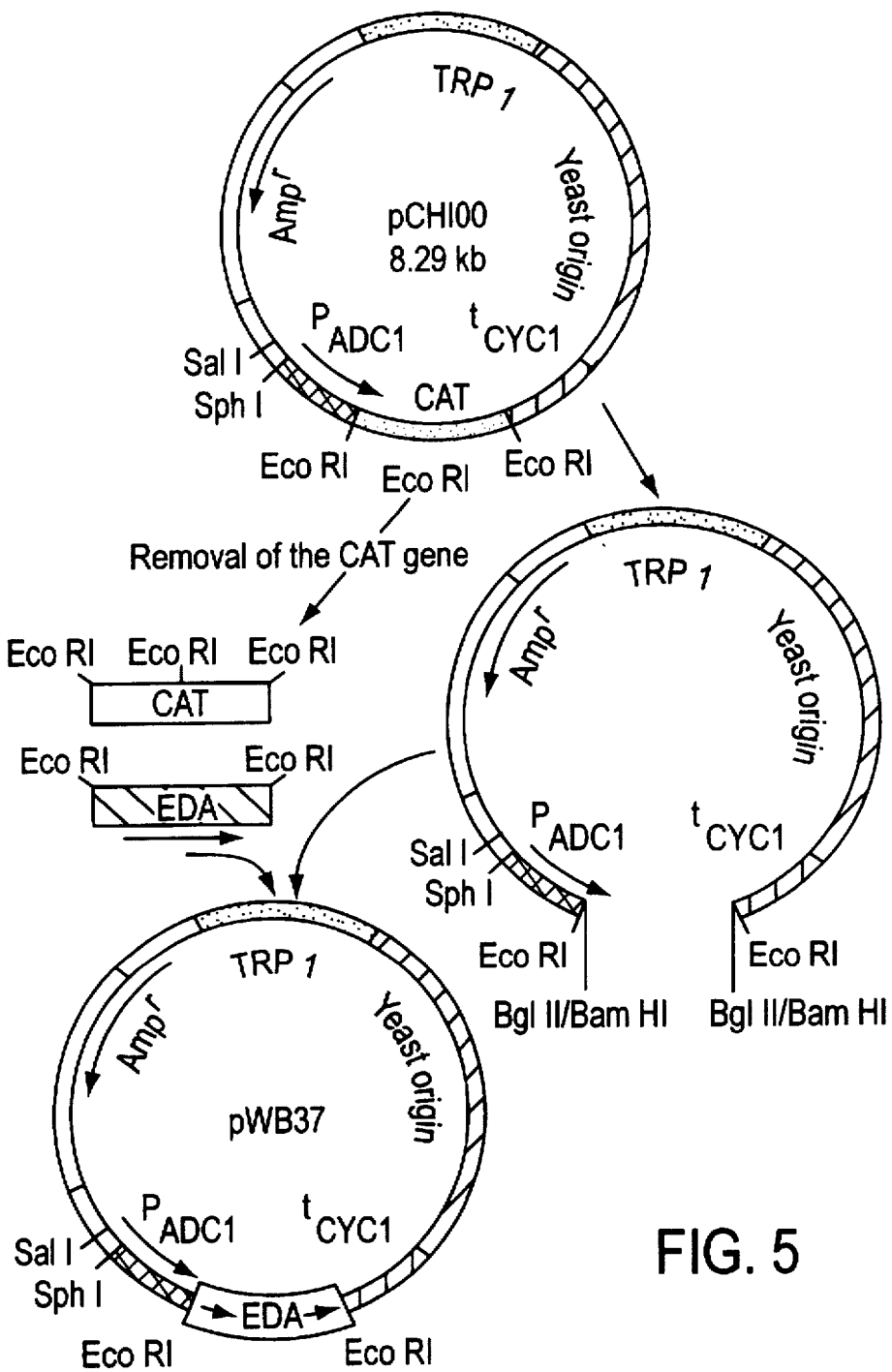
FIG. 5 is a schematic representation of the steps involved in the construction of an eda yeast expression vector.

The reactions were incubated at 37° C. for 3 hours. The reactions were then analysed by flat-bed agarose gel electrophoresis. Plasmids with the eda fragment inserted in the correct orientation yielded an 800 base pair fragment while the incorrect orientation yielded a 1050 base pair fragment (FIG. 5). Correctly oriented plasmids were designated pWB37.

Amplification of the edd open reading frame

Using polymerase chain reaction (PCR) the complete coding sequence of the edd gene was sub-cloned into the bacterial vector pKK223-3 using newly introduced EcoRI sites flanking the two genes. The following oligonucleotides were synthesised using an Applied Biosystems ABI381A DNA synthesiser.

```
native    5'GACAACTCAATTTCAGGAGCCTTTATGAAT3'
synthetic 5'GACAACTCGAATTCAGGATCCAAAATGAAT3'
              EcoRI    BamHI native    5'CCTGATTACAAATTTGTCGTCTTAAAAGT3'
synthetic 5'CCTGAATTCAAATTTGTCGTCTTAAAAGT3'
              EcoRI
```

The above primers were designed so as to change the 3 bases upstream of the ATG start codon into A. This would improve the efficiency of expression of the gene in yeast. The following PCR reaction conditions were used to amplify the edd gene from purified Clone 2 DNA. Purified Clone 2 DNA (50 ng), 0.4 mg of each of the synthetic oligonucleotides, PCR reaction buffer 10x (Perkin-Elmer), 2 units of Tag polymerase (Perkin-Elmer), water up to 100 µl and PCR grade mineral oil (60 µl) were mixed in a 0.5 ml microcentrifuge tube. A Perkin-Elmer thermal cycler was used with the following cycle conditions: 1st cycle, 92° C. for 2 minutes; 2nd cycle, 92° C./2 minutes 53° C./3 minutes 72° C./2 minutes; followed by a further 28 cycles at 90° C./2 minutes 53° C./3 minutes 72° C./2 minutes. The amplified edd DNA was purified by flat-bed agarose gel electrophoresis (Maniatis et al 1982 p. 159). The 1800 base-pair fragment was excised from the gel and purified by electroelution using an IBI electroelution unit. DNA capture and precipitation was with 3M sodium acetate-ethanol as described in the manufacturer's instructions. The DNA was centrifuged at 13000 rpm at 4° C. in a MSE Microcentrifuge for 10 minutes. The supernatant was carefully removed and 500 µl of 70% v/v ethanol was added to the DNA. The sample was carefully mixed and the contents recentrifuged as previously. Following a second 70% v/v ethanol addition and centrifugation, the DNA was dried and resuspended in 6 µl of sterile water, 2 µl of 10x restriction buffer C (IBI) and 20 units of EcoRI restriction endonuclease (IBI) then incubated in a water bath at 37° C. for 3 hours. After 60 minutes 2 µl of 40 mM spermidine was added to the reaction mixture. The mixture was purified again using flat-bed gel electrophoresis and electroeluted as previously.

Construction of the edd bacterial expression vector

Ligation of the DNA fragment containing the edd coding region into plasmid pKK223-3 was performed in the following reaction mix:

| edd PCR fragment | 1 µl (300 mg) |
| pKK223-3 EcoRI cleaved | 2 µl (200 mg) |
| 10 × ligation buffer (Pharmacia) | 1 µl |
| T4 DNA ligase (Pharmacia) | 0.5 µl |
| 1 mM ATP | 1 µl |
| H₂O | 4.5 µl |

The above reaction was incubated at 15° C. for 16 hours and then diluted to total volume of 50 µl. The ligation mixture was used to transform JM109 exactly as described previously (Maniatis et al 1982 p.250). Transformants were selected by growth at 37° C. for 24 hours on LB agar supplemented with ampicillin (50 µg/ml). Randomly selected transformants were analysed for the presence of the edd insert in the correct orientation in pKK223-3. Plasmid isolations were conducted as described previously (Maniatis et al 1982 p.250). The insert orientation was determined by cleaving 300 ng of plasmid DNA with SmaI restriction endonuclease (10 units) in a total reaction volume of 20 µl containing 2 of 10x reaction buffer E (IBI). Following incubation at 37° C. for 3 hours the fragments so generated were analysed by flat-bed agarose gel electrophoresis (Maniatis et al 1982 p.159). Correctly oriented clones yielded a 1332 base pair fragment while the incorrect orientation resulted in a 480 base-pair fragment. The correctly oriented plasmid was designated pKEDD (FIG. 6).

DNA sequencing of the PCR amplified edd clone in pKKEDD was conducted, and errors were found. These errors changed a lysine (AAA) codon into a stop codon (TAA) (position 931 in FIG. 2). The edd coding sequence was repaired using the scheme shown in FIG. 7.

The EcoRI fragment containing the edd gene from pKKEDD was cleaved out by digestion with EcoRI as described previously. Also the vector pIC19R was digested with EcoRI. The restricted fragments were separated by flat-bed agarose gel electrophoresis (Maniatis et al 1982 p.159). The 180 base pair fragment containing the edd gene and the linearised pIC19R were electroeluted using an IBI electroelution unit and 3M sodium acetate exactly as described in the manufacturer's instructions. The DNA was pelleted by centrifugation at 13,000 rpm at 4° C. and the supernatant removed. 70% vv ethanol (500 µl) was added to the DNA and gently agitated. Following recentrifugation to repellet the DNA the ethanol was removed and the DNA was dried to remove traces of ethanol. The DNA was resuspended in 10 µl of sterile distilled deionised water. The linearised PIC19R vector and the DNA fragment containing the edd gene were ligated together using the following reaction mixture (Maniatis et al 1982 p.392):

| edd DNA | 5 µl (300 ng) |
| pIC19R EcoRI cleaved | 2 µl (200 ng) |
| 10 × ligation buffer | 1 µl |
| T4 DNA ligase | 0.5 µl |
| 10 mM ATP | 1 µl |
| Water | 0.5 µl |

The reaction was incubated at 15° C. for 16 hours. Following ligation the mixture was diluted to 100 µl with 5 µl 20×SSC (Maniatis et al 1982) and 85 µl of sterile distilled and deionised water. The E. coli strain JM109 was transformed exactly as described in Maniatis et al 1982 p.250). The transformants were selected on LB agar supplemented with ampicillin (50 µl/ml) and 5-bromo-4-chloro-3-iodo-BD-galactopyranoside (X-Gal) 0.15 mg/ml and isopropyl-BD-thiogalactopyranoside (IPTG) 0.25 mg/ml. Incubation of the selection media was at 37° C. for 24 hours. Possible clones were selected by their white appearance on the above media.

Small-scale plasmid isolations (Maniatis et al 1982 p.368) were carried out on randomly selected white colonies possessing pIC19R into which the edd gene had been inserted. Cleavage with restriction endonucleases Sph1 and Acc1 removed the central (1545 base pair) section of the edd gene which contained the PCR-induced mistakes in the edd nucleotide sequence. Plasmid DNA of Clone 1 (FIG. 2) was isolated as above and digested with restriction enzymes Sph1 and Acc1 to cleave the central region native edd DNA. The digested DNA was separated using flat-bed agarose gel electrophoresis (Maniatis et al 1982 p.159). The fragment of the edd DNA cleaved from Clone 1 and the 2955 base-pair fragment of pICEDD containing the 'ends' of the edd gene were excised from the gel and purified by electroelution, as described previously.

The two fragments were ligated together by the following reaction:

| pICEDD1 DNA (SphI/AccI) | 4 µl (300 ng) |
| edd DNA (SphI/AccI) | 3 µl (200 ng) |
| 10 × ligase buffer (Pharmacia) | 1 µl |
| T4 DNA ligase (Pharmacia) | 1 µl |
| 10 mM ATP | 1 µl |

The above reaction was incubated at 15° C. for 16 hours and then diluted to a total volume of 50 µl with sterile distilled deionised water. The ligation mixture was transformed into E. coli strain JM109 as previously described (Maniatis et al 1982). Transformants were selected on LB agar supplemented with 50 µl/ml ampicillin. Of the 450 transformants, 100 were replated onto LB agar supplemented with 50 µl/ml ampicillin. Twenty of these replated transformants were selected at random and small-scale plasmid isolations prepared from them (Maniatis et al 1982 p.368). These plasmids (300 ng of each) were digested with EcoRI (20 units), in a total reaction volume of 20 µl containing 2 µl of 10x reaction buffer C (IBI). The reactions were incubated at 37° C. for 3 hours before analysis by flat-bed agarose gel electrophresis (Maniatis et al 1982 p.159).

Recombinant plasmids which contained a 1800 base-pair EcoRI generated fragment, contained the edd DNA from Clone 1 ligated into the PCR generated 'ends' of the edd gene. This plasmid was designated pICEDD1.

Construction of the edd yeast expression vector

All attempts to clone the edd gene open reading frame next to either a bacterial (tac) or a yeast/bacterial promoter (ADH1) failed. Only clones with the reverse orientation with respect to the promoter were obtained. This difficulty arose due to the toxicity of 2-keto-3-deoxy-6-phosphogluconate (KDPG), a chemical made as a result of the activity of the enzyme 6-phosphogluconate dehydratase, the latter being the product of the edd gene expression.

In order to overcome the toxicity problem, the edd gene open reading frame was cloned downstream of the extremely tightly regulated yeast promoter THI4 (Praekelt et al 1994). As an added precaution, this new shuttle vector was transformed into an $E.$ $coli$ strain harbouring the eda expression vector. The gene product of eda splits the KDPG into pyruvate and glyceraldehyde-3-phosphate which are non-toxic. This strategy required the designing of the edd shuttle vector such that it carried selectable markers for both $E.$ $coli$ and yeast that were different from those on the eda containing plasmid. FIG. 8 shows the stepwise construction of this vector (pFLAN10).

The pFLAN1 vector shown in FIG. 8 was first derived from pFL38. A 18 base-pair fragment of the latter was removed using SalI and HindIII as follows:

| pFL138 purified DNA | 4 µl (500 ng) |
|---|---|
| SalI (10 units) | 1 µl |
| HindIII (10 units) | 1 µl |
| 10 × reaction buffer A | 2 µl |
| Water | 12 µl |

Incubation of the reaction mixture was at 37° C. for 3 hours. After 60 minutes 2 µl of 40 mM spermidine was added. The reaction mixture was purified by flat-bed agarose gel electrophoresis, electroelution and 70% v/v ethanol washed (exactly as described previously). The ADH1 promoter/CYC1 terminator cassette from pCH98 (C Hadfield et al 1987) was cleaved from this vector by digesting 500 ng of the vector with 1 µl (10 units) of SalI and 1 µl (10 units) of HindIII 2 µl of 10x reaction buffer A (IBI) in a total volume of 20 µl. Incubation was for 3 hours at 37° C. with 2 µl of 40 mM spermidine being added after 60 minutes. The digest was analysed by flat-bed agarose gel electrophoresis. The 1100 base-pair fragment was excised from the gel; purified by electroelution and 70% v/v ethanol washed as previously described.

The 1100 base-pair fragment ADH1 promoter/CYC1 terminator was ligated into the linearised pFL38 using the following reaction: pFL38 purified as above, 2 µl (200 ng), ADH1/CYC1 fragment 4 µl (300 ng), 10x ligase buffer (Pharmacia) 1 ml, T4 DNA ligase (Pharmacia) 1 µl, 10 mM ATP 1 µl was incubated at 15° C. for 16 hours and subsequently diluted to 50 µl with sterile distilled deionised water. The ligation mixture was used to transform $E.$ $coli$ strain JM109 (Maniatis et al 1982 p.250). Six transformants were detected following growth on LB agar supplemented with 50 µl/ml ampicillin. Small-scale plasmid isolations were performed on the six transformants (Maniatis et al 1982 p.250). Digestion of the plasmid DNA was conducted as follows: Transformant DNA 300 ng with 1 µl (10 units) SalI, 1 µl (10 units) HindIII, 2 µl reaction buffer A (IBI) made up to 20 µl with sterile distilled deionised water was incubated at 37° C. for 3 hours. Analysis by flat-bed agarose gel electrophoresis was conducted exactly as described previously. All six of the transformants obtained were found to contain the 1100 base-pair ADH1/CYC1 fragment. This plasmid was designated pFLAN1 (FIG. 8).

The plasmid pFLAN6 was generated as follows: Plasmid pFLAN1 DNA (300 ng) was digested with restriction endonuclease Xmn1 (1 µl, 10 units). This unique cleavage site is within the ampicillin resistance gene of pFLAN1. The 1300 base-pair fragment containing the Kanamycin resistance gene from GenBlock plasmid (Pharmacia) was cleaved by digestion of 300 ng of GenBlock DNA with 10 units of HincII restriction enconuclease in 1×reaction buffer A (IBI). The restriction fragments from both reactions were separated by flat-bed agarose gel electrophoresis as described previously. The linearised pFLAN1 plasmid and the 1300 base-pair fragment from GenBlock were excised from the gel and purified using CTAB/butanol exactly as described by Langridge et al 1980. The two purified fragments were ligated together as follows: pFLAN1 DNA (200 ng) 1300 base-pair kanamycin resistance gene-containing fragment (200 ng), 10x ligase buffer (Pharmacia) 1 µl, T4 DNA ligase (Pharmacia) (1 µl), 10 mM ATP (1 µl) made up to 10 µl with sterile distilled, deionised water. The reaction mixture was incubated for 16 hours at 15° C. and subsegently diluted to 50 µl with sterile distilled deionised water. The ligation mixture was used to transform $E.$ $coli$ strain JM109 exactly as described in Maniatis et al 1982 p.250. Transformants were selected on LB agar supplemented with 50 µl/ml kanamycin. The selective agar was incubated at 37° C. for 24 hours. Loss of ampicillin resistance was confirmed by replating the transformants onto LB agar supplemented with 50 µl/ml ampicillin.

The 433 base-pair ADH promoter of pFLAN6 (300 ng) was removed by digestion with EcoRI (10 units) in a total reaction volume of 20 µl containing 2 µl of 10x reaction buffer A. Following 3 hours incubation at 37° C. the restricted fragments were separated by flat-bed agarose gel electrophoresis as described previously. The 6577 base-pair fragment was excised from the gel and purified using the CTAB/butanol method as described by Langridge et al 1980. The EcoRI generated 1800 base-pair fragment containing the edd from plasmid pICEDD1 by cleaving 300 ng of pICEDD1 DNA with 10 units of EcoRI in a total reaction volume of 20 µl containing 2 µl of 10 x reaction buffer A. Again the 1800 base-pair fragment was separated by flat-bed agarose gel electrophoresis (described previously). The band was excised and purified using the CTAB/butanol method (Langridge et al 1980). Both isolated fragments were resuspended in 6 µl of distilled deionised water. The two fragments were ligated together in the following reaction: pFLAN6 DNA (200 ng), 1800 bp edd fragment (300 ng), 10x ligase buffer (Pharmacia) 1 µl), T4 DNA ligase (Pharmacia) (1 µl), 10 mM ATP (1 µl) made up to 10 µl with sterile distilled, deionised water. The ligation mixes were incubated at 15° C. for 16 hours and then diluted to 50 µl with sterile distilled deionised water. This ligation mixture was used to transform $E.$ $coli$ strain JM109 exactly as described previously. Transformants were selected by growth at 37° C. for 24 hours on LB agar supplemented with 50 μl/ml kanamycin. Plasmid isolations were carried out on randomly selected transformants (Maniatis et al 1982 p.250) and 500 ng of each plasmid was digested with BamHI (10 units) and HindIII (10 units) in a total reaction volume of 20 μl containing 2 μl of 10x reaction buffer A. The reactions were incubated at 37° C. for 3 hours followed by analysis of the restricted fragments by flat-bed agarose gel electrophoresis (described previously). Plasmids with the edd gene in the correct orientation produced a restriction fragment of 2200 base pairs. This plasmid was designated pFLAN8.

The tightly-regulated yeast promoter, the THI4 promoter was removed from pWB20 by digesting 35 μg of pWB20 DNA with 50 units of EcoRI in T4 polymerase buffer in a total volume of 150 μl. After overnight incubation at 37° C., dNTPs were added plus 10 units of T4 polymerase and the mixture incubated at 37° C. for 60 minutes, to "blunt-end" the DNA. The microcentrifuge tube was then incubated at 75° C. for 10 minutes to inactivate the enzyme. The DNA was cleaned up using the Promega Wizard DNA clean up method. The DNA was then digested with 50 units of HindIII in a total volume of 200 μl. After incubation at 37° C. for 90 minutes, 40 μl of loading dye (bromophenol blue) was added and the total volume loaded into a 1% w/v low melting point (LMP) agarose gel. The 1.1kb HindIII-EcoRI fragment was purified from the gel using the Promega Wizard clean up method (see manufacturer's instructions). Recovered DNA was precipitated with ethanol and redissolved in TE to a final DNA concentration of 50–200 μg ml$^{-1}$.

pBSKS (20 μg) was then digested with 50 units of HindIII (at 37° C. for 90 minutes) and 50 units of SmaI (at 30° C. for 90 minutes) in a total volume of 150 μl. 40 μl of gel loading dye was added and the total volume loaded onto a 1% w/v LMP agarose gel. The large, 4.0kb fragment was then purified using the Promega Wizard system. Ligation of the purified THI4 promoter fragment and the digested pBSKS fragment was carried out as follows. 100 ng of pBSKS DNA and 250 ng of THI4 promoter fragment DNA were mixed with 4 units of T4 DNA ligase and 1 μl of 10x ligase reaction buffer in a total volume of 10 μl. The ligation reaction was incubated at 16° C. for 16 hours. 5 μl of the ligation mix was then used to transform 200 μl of competent JM109 cells. Transformants were selected as white colonies growing on LB agar supplemented with ampicillin, Xgal and IPTG. 200 colonies per plate grew up, of which 85% were white. White colonies (6) were picked and small-scale plasmid preparations were made. These plasmid DNAs were digested with HindIII and BamHI. The digested plasmids were analysed on a 1% agarose gel. All six contained the 1.1kb THI4 plasmid fragment. One of the six was isolated and designated pBSKS36.

40 μg of pBSKS36 DNA was then digested with SalI (40 units) in 10x T4 DNA polymerase buffer overnight at 37° C. 10 units of T4 DNA polymerase was then added and the mixture incubated at 37° C. for 60 minutes. The microcentrifuge tube was then incubated at 75° C. for 10 minutes to inactivate the enzyme. The DNA was cleaned up using the Promega Wizard DNA clean up method. It was then digested with BamHI (40 units) with incubation at 37° C. for 60 minutes. 40 μl of gel loading dye was then added and the total volume run on a 1% w/v LMP agarose TBE gel. The 1.1kb THI4 promoter DNA fragment was purified from the gel using the Promega Wizard DNA method.

27 μg of pFLAN8 DNA was digested with 40 units of AatII in 10x T4 polymerase buffer overnight at 37° C. 10 units of T4 DNA polymerase was then added and the mixture incubated at 37° C. for 60 minutes. The microcentrifuge tube was then incubated at 75° C. for 10 minutes to inactivate the enzyme. The DNA was cleaned up using the Promega Wizard DNA method. The linearised DNA was then re-digested with BamHI (40 units) at 37° C. for 60 minutes. This removes a 400 bp fragment. The large vector fragment was isolated on a 1% w/v LMP agarose gel and purified using the Promega Wizard DNA Method. 100 ng of this pFLAN8 vector DNA plus 250 ng of the THI4 promoter fragment (SalI-blunted/BamHI) were ligated using 4 units of T4 DNA ligase plus 1 μl of 10x ligase buffer in a total volume of 10 μl. This mixture was incubated at 16° C. overnight. 5 μl of this ligation mix was used to transform 200 μl of competent JM109 cells. Transformants were selected for growth on LB agar supplemented with kanamycin; 12 colonies per plate were obtained. These were screened by small scale plasmid preparation. 10% of these were shown to contain the THI4 promoter insert by restriction analysis. One of these was isolated and designated pFLAN10.

pFLAN10 proved to be stable in *E. coli* by itself, hence there was no need to introduce pFLAN10 into an *E. coli* strain harbouring the eda expression vector. However, all attempts to introduce both plasmids (pFLAN10 and pWB37) together into yeast proved unsuccessful, yielding no transformants. Hence it was decided to construct a single vector containing both the eda and edd expression cassettes.

Construction of the eda-edd Yeast Expression Vector

The edd expression cassette (containing the THI4 promoter, the edd coding sequence and the CYC1 terminator) was released from pFLAN10 as a 3.5kb HindIII fragment as follows:

| Digest | |
|---|---|
| pFLAN10 DNA | 10 μl (20 μg) |
| 10x Reaction buffer A | 2 μl |
| 1XTE | 6 μl |
| HindIII | 2 μl (20 units) |

The reaction mixture was incubated at 37° C. for 60 minutes. 2 μl of 10x agarose gel loading buffer was added to the mixture, which was then purified by horizontal agarose gel electrophoresis on a 0.6% w/v agarose TBE gel run at 15V for 16 hours. The 3.5kb fragment was excised from the gel using a razor blade. The DNA was purified using the QIAEX DNA Gel Extraction Kit (Qiagen Inc, CA, USA) exactly as described in the manufacturer's instructions. pWB37 was also digested with HindIII.

| Digest | |
|---|---|
| pWB37 DNA | 12 μl (3.6 μg) |
| 10x Reaction buffer A | 2 μl |
| 1XTE | 5 μl |
| HindIII | 1 μl (10 units) |

The reaction mixture was incubated at 37° C. for 60 minutes. 1 μl of 10x agarose gel loading buffer was then added and the digest analysed by horizontal agarose gel electrophoresis on a 0.6% w/v agarose TBE gel run at 15V for 16 hours. The large, 6.0kb fragment of pWB37 was then excised from the gel and the purified using the Geneclean II kit (BIO, Inc., USA) exactly as described in the manufacturer's instructions.

The purified 6.0kb pWB37 HindIII fragment and the purified 3.3kb pFLAN10 HindIII fragment were then ligated together as follows:

| Ligation | |
|---|---|
| Purified 6.0kb pWB37 HindIII fragment DNA | 5 µl (1 µg) |
| Purified 3.3kb pFLAN10 HindIII fragment DNA | 10 µl (2 µg) |
| 10x ligation buffer (Pharmacia) | 2 µl |
| 10 mM ATP | 2 µl |
| T4DNA ligase (Pharmacia) | 1 µl |

The reaction mixture was then incubated at 16° C. for 16 hours. The ligation mixture was used to transform competent cells of E. coli strain DH5a (Hanahan 1983, Bethesda Research Laboratories, 1986) exactly as described previously (Maniatis et al 1982, p. 250).

Transformants were selected by growth at 37° C. for 24 hours on LB agar supplemented with ampicillin (100 µg ml$^{-1}$). Thirty transformants grew up on these selective plates. These were picked and small scale plasmid isolations prepared from them exactly as described previously (Maniatis et al 1982, p. 368).

These plasmids were digested with HindIII as follows:

| Digest | |
|---|---|
| Plasmid DNA | 10 µl (approx. 2 µg) |
| 10x Reaction buffer A | 2 µl |
| 1XTE | 7 µl |
| HindIII | 1 µl (10 units) |

The reaction mixtures were incubated at 37° C. for 60 minutes, 2 µl of 10x agarose gel loading buffer was then added and the digests analysed by horizontal agarose gel electrophoresis on a 0.8% w/v agarose TBE gel run at 100V for 3 hours. Five recombinant plasmids were identified which contained the 6.0kb pWB37 HindIII fragment and the 3.3kb pFLAN10 HindIII fragment. These five transformants were replated onto LB agar supplemented with ampicillin at 100 µg ml$^{-1}$ and incubated at 37° C. for 24 hours. A single colony from each of the five plates was then picked and used for small-scale plasmid preparations exactly as described previously (Maniatis et al 1982, p.368). These plasmids were then digested with SphI to determine the orientation of the edd cassette with respect to the eda cassette in the recombinant plasmids.

| Digest | |
|---|---|
| plasmid DNA | 10 µl (approx 2 µg) |
| 10x reaction buffer | 2 µl |
| 1XTE | 7 µl |
| SphI | 1 µl (10 units) |

The reaction mixtures were incubated at 37° C. for 60 minutes, 2 µl of 10x agarose gel loading buffer was then added and the digests analysed by horizontal agarose gel electrophoresis on a 0.8% w/v agarose TBE gel at 15V for 16 hours. All five recombinant plasmids show the same orientation of insertion for the edd cassette: it lies in the same transcriptional orientation as the eda cassette. Plasmids with the genes in this orientation yield 6.7kb and 2.6kb SphI fragments. This plasmid is designated pWB44; see FIG. 9.

Transformation of Yeast Strain with the eda-edd yeast expression vector

A strain 37.1.6 is MATa ura3-52 leu2 trp1 pfk1-1 pfk2::LEU2. It is not able to grow on glucose.

The existence of both a pfk1 and a pfk2 mutation in strain 37.1.6 was confirmed by mating it to strain 34.1.6 (MATα leu2 trp1 pfk1Δ1 pfk2::LEU2). These strains were mated together on YEPG agar (which permits the growth of both haploids) and after due time were replicated to YEPD agar. Nothing grew, indicating that not a single functional PFK gene existed in either haploid. The mating competence of both strains was simultaneously proven using appropriate mating testers.

During the construction of pWB44 the yeast ARS sequence required for autonomous plasmid maintenance and part of the trp1 gene at the 3' end were removed and replaced by the edd expression cassette. This means that for the maintenance of pWB44 in yeast it must integrate into the chromosome and that it has no obvious yeast selectable marker. Selection for maintenance of the integrated plasmid pWB44 could be made on glucose medium if both eda and edd cassettes were expressed in yeast. Therefore a strategy was devised to transform yeast strain 37.1.6 with pWB44 DNA and select for transformants on YEPD agar. The 5' portion of the trp1 coding sequence present on pWB44 represents the largest segment of yeast DNA sequence on the plasmid and hence the most likely crossover point for integrative recombination into the yeast chromosome.

The transformation of yeast strain 37.1.6 with plasmid pWB44 DNA was carried out as follows: A loopful of 37.1.6 cells were scraped from an agar plate and transferred to a microcentrifuge tube containing 0.5 ml YEPGE. This was then pelleted in a microcentrifuge at room temperature for 10 seconds. The supernatant was decanted by inverting the tube and shaking it once. 10 µl (100 µg) of carrier DNA—sonicated, denatured salmon testes DNA (Sigma)—plus 10 µl (approx 2 µg) of uncut pWB44 DNA (isolated as described previously by small-scale plasmid preparation) were then added and subjected to vortex mixing. 0.5 ml of freshly prepared PEG/lithium acetate/TE mix (9 ml filter-sterilised 45% w/v PEG4000 (Sigma), 1 ml 1M lithium acetate, 0.1 ml 1M Tris-HCl pH 7.5, 0.02 ml 0.5M EDTA) was then added and vortexed to mix. The centrifuge tube was then incubated at room temperature for 16 hours.

100 µl of the mixture was spread directly onto YEPD agar. Plates were incubated at 21° C. for 14 days. Twelve yeast colonies grew on the YEPD agar. These were picked and replated onto YEPD agar and incubated at 21° C. for 6 days. Evidence to verify the presence of eda and edd in 37.1.6, the orientation of eda and edd with respect to each other and the site of integration of pWB44 were obtained by a series of PCR experiments. See FIG. 10 for an overview of the PCR strategies.

To verify the presence of the eda expression cassette in all twelve 37.1.6 transformant candidates, oligonucleotide primers were used that hybridise to sequences at the 5' end and 3' end respectively of the eda expression cassette amplification. All twelve transformants showed the presence of a 700 bp eda fragment, whereas no such fragment is present in the negative control 37.1.6.

To verify the presence of the edd gene in the 37.1.6 transformant candidates, primers were used that hybridise to sequences within the edd coding region. On amplification, all twelve transformants showed the presence of a 1kb edd fragment, whereas no such band was present in the negative control 37.1.6.

To check the orientation of the eda and edd genes in the transformants, primers were used that respectively hybridise to a sequence in eda and to a sequence in edd. On amplification of three of the twelve transformants, picked at random for this test, all three showed the presence of a 3.5kb fragment which spans the eda-edd genes whereas no such band was present in the negative control 37.1.6. This confirms that the eda and edd genes are present in the transformants in the same transcriptional orientation and are adjacent, as expected.

The 5' portion of the trp1 coding sequence present on pWB44 is the largest sequence of yeast DNA present in the plasmid and hence was judged the most likely site for crossover during the integration of pWB44, into the yeast chromosome. To verify that trp1 is the site of integration of pWB44 the oligonucleotide primers were used that hybridise respectively to an internal eda gene sequence and to a sequence present in the chromosomal copy of trp1, which is not present on the portion of trp1 in pWB44. On amplification of four transformants picked for this test, all showed the presence of the 4.8kb eda-trp1 fragment. No such band was present in the negative control 37.1.6, nor in the pWB44 plasmid DNA which was also tested. This confirms that pWB44 has integrated at the trp1 locus in yeast strain 37.1.6.

Small-Scale Fermentation

Laboratory scale fermentations were carried out to assess the fermentation performance of the 37.1.6 transformants in minimal medium plus glucose and in commercially- available Munton and Fison's brewing wort. Minimal medium plus glucose is Difco yeast nitrogen base (YNB) 0.67% w/v plus glucose 10% w/v. This solution was sterilised by autoclaving for 20 minutes. 500 ml of YNB-glucose was then added to a cleaned, sterilised tall-tube with Suba-seal attached. Pitching yeast was grown up aerobically (H54-2B a laboratory wild-type and DFY70 (relevant genotype pfk1-1) in YEPD and 37.1.6 and 37.1.6/pWB44 in YEPGE) for 3–4 days with shaking at 21° C. to yield sufficient crop. 10 g spun yeast of each strain was then added to the appropriate tall tube and a rubber bung fitted with an air-lock was fitted to the top of each tube. Tall-tubes were then incubated at 21° C. Specific gravity was monitored during fermentations by transferring 2 ml samples to the Anton Paar density meter. The fermentation profile is shown in FIG. 11. When fermentation was complete, samples were removed for ethanol determination by GC and sugar analysis by HPLC. The remaining contents of each tall tube were transferred to a centrifuge tube and the yeast collected by centrifugation at 1000×g for 10 minutes. The supernatant was removed, the pots drained and the yeast crop weighed. Results of the ethanol and sugar analyses and the yeast crop measurements are summarised in Table 2. From these results and the profiles in FIG. 11 it is clear that 37.1.6/pWB44 is capable of fermenting glucose to produce ethanol with great efficiency, producing a minimal yeast crop.

37.1.6/pWB44 cropped from the fermentation in YNB-glucose was then used to pitch into tall-tubes containing 500 ml of Munton and Fison's ale wort. This hopped wort was prepared by boiling wort concentrate in water for 5 minutes and then diluting to the required specific gravity of 1060°. It was then autoclaved for 20 minutes. When cooled, the wort was transferred to a 10 l flask and aerated steadily through a glass sinter for 45 minutes. 500 ml of aerated wort was then added to a cleaned, sterilised tall-tube with Suba-seal attached. 10 g spun yeast (see above) was resuspended in 10 ml wort prior to pitching. 3 ml (approximately 3 g) of yeast was then added to the tall tube and a rubber bung fitted with an air-lock was fitted to the top of the tube. Tall-tubes were then incubated at 21° C. Specific gravity was monitored during fermentation as described above. The fermentation profile is shown in FIG. 12. When fermentation was complete, samples were removed for ethanol determination by GC and sugar analysis by HPLC. The remaining contents of each tall-tube were transferred to a centrifuge pot and the yeast collected by centrifugation at 1000×g for 10 minutes. The supernatant was removed, the pots dried and the yeast crop weighed. Results of the ethanol and sugar analyses and the yeast crop measurements are summarised in Table 3. From these results it is clear that 37.1.6/pWB44 can ferment efficiently to produce ethanol whilst yielding a low yeast crop. The residual sugars are predominantly maltose reflecting the fact that 37.1.6 is a laboratory yeast strain, less well adapted to maltose utilisation than a brewing strain.

Table 4 shows a comparison of growth efficiencies of the 37.1.6/pWB44 yeast compared with 7 different commercial yeast strains. In all cases yeasts were grown in Munton & Fison ale wort. It is quite clear that to produce a given amount of ethanol much less yeast biomass is produced using the yeast described in this invention than is produced by 'standard' yeast strains.

Immobilised Fermentation Trials

Approximately 15 l (60×250 ml flasks) of 37.1.6/pWB44 in YEPGE was grown at 21° C. shaking for 3–4 days. The flasks were transferred to 4° C. and the yeast allowed to settle naturally. Most of the supernatant was then decanted from each flask such that the total final volume of yeast slurry was reduced to approximately 3 l. This was then stored at 4° C. prior to loading onto the reactor.

The reactor was cleaned by soaking in hot DECON 90 for 24 hours; the DECON was drained and the reactor rinsed with several changes of hot water. Siran glass beads (1540 ml) were added to the reactor, which was then sterilised by recirculating ethanol (70% v/v) through the system. The is ethanol (8 liters) was drained from the reactor and replaced with brewing wort.

Part of the wort (3 liters) was drained from the reactor and replaced with the same volume of yeast slurry. The system was fluidised and run on a batch basis at 25° C. for 4 days. When the wort gravity reached 1005°, the wort pump was switched on and the gravity within the reactor controlled to 1010° by feedback control of wort pump speed from the fermentation control package. The reactor was maintained at 20° C. during operation.

A profile of the gravity reading taken during this period showed a stable output.

Analysis of metabolism in 37.1.6/pWB44 using $^{13}$C nuclear magnetic resonance A loopful of strain 37.1.6/pWB44 was inoculated into 100 ml of YEPG medium in a 250 ml conical flask and incubated in a gyrorotatary incubator (180 rpm) at 30° C. for 72 h when the optical density of the cult-are measured at 600 nm ('OD$_{600}$') was 4.5. 5 ml of this was transferred to 95 ml of fresh YEPG medium in a 250 ml conical flask. These cells were incubated at 30° C. in the gyrorotatary incubator for 23 h when the OD$_{600}$ was observed to be 3.2. It was known from earlier studies in which this strain was cultivated under the same conditions in YEPG medium and the OD$_{600}$ was recorded at regular intervals that when the OD$_{600}$ was 3.2 the cells were in exponential phase of growth (data not shown). The cells were sedimented by centrifugation and, the growth medium poured away. The cells were then resuspended in 100 ml of YEPD medium and incubated in the same gyrorotatary incubator at 30° C. in a 2 l conical flask. The reason for using such a large flask in relation to the volume of culture incubated was to ensure that the cells received a plentiful supply of oxygen. After 72 h incubation the OD$_{600}$ was 3.28. The cells were then collected by centrifugation at 30° C., the medium was decanted and the cells were resuspended in 2 ml of YEP which had been pre-warmed to 30° C. and transferred to a 50 ml conical flask. A solution of 70.3 mg of [2-$^{13}$C]-glucose in the minimum quantity of sterile distilled water to dissolve the glucose which had been prepared 2 h previously and kept at 30° C., was then added to the cells. The reason for preparing the glucose well in advance of the experiment was to allow establishment of the equilibrium between the β and α anomers of glucose. This culture containing the 'labelled' glucose was shaken for 24 h in the same gyrorotatary incubator. At the end of this time, the cells were harvested by centrifugation in a microcentrifuge at 11,600 g for 30 sec. The growth medium was decanted and then 300 μl of ice-cold 20% (w/v) perchloric acid was added to the cells which were vortexed violently for 1 min. The tube containing the 37.1.6/pWB44 cells and the perchloric acid was placed in ice for 1 h. At 15 min intervals the contents of the tube were vortexed thoroughly. This treatment kills the cells rapidly and causes small molecules to be extracted from the yeast cells into the perchloric acid and has been used successfully in the past for this sort of study (Dickinson & Hewlins 1988; Dickinson & Hewlins 1991; Dickinson et al 1995). After 1 h the contents were vortexed again and then centrifuged at 11,600 g for 30 sec in a microcentrifuge at 4° C. This sedimented the perchloric acid-denatured materials. The whole of the supernatant (perchloric acid-soluble materials) was carefully removed to a fresh microcentrifuge tube which was standing in ice and then just enough ice-cold 2M potassium hydroxide was added to neutralise the perchloric acid extract (ie. shift to pH=7.0). This procedure has the added advantage of producing potassium perchloric as a white precipitate. The neutralised extract was stored in ice for 1 h and vortexed at 15 min intervals. After 1 h the pH was re-checked and found to be 7.0 and then the potassium perchlorate was sedimented by centrifugation in a microcentrifuge at 11,600 g for 30 see at 4° C. The clear supernatant (500 μl) was carefully removed to a new tube and then 30 μl of 1M phosphate buffer pH=6.00 was added and then 100 μl of $^2$H$_2$O. This was then analysed in a Bruker WM360 NMR spectrometer operating at 90.5 MHz as described previously (Dickinson & Hewlins 1988; Dickinson & Hewlins 1991; Dickinson et al 1995). The spectrum was recorded for the solution in a 5 mm NMR tube, using 32K data points over 22,000 Hz, with broad-band $^1$H decoupling. All chemical shifts are reported in ppm relative to the signal for sodium 3-(trimethylsilyl)propane-1-sulphonate (assigned δ=0) measured in $^2$H$_2$O solution as the external standard.

A considerable number of resonances were observed. Only four resonances that have a major bearing on interpreting the carbon metabolism of strain 37.1.6/pWB44 are described here. These were due to C-2α of fructose-6-phosphate ('F-6-P') (107.5 ppm), C-2β of F-6-P (104.4 ppm), C-3α of the furanose form of F-6-P (84.7 ppm) and C-3β of the furanose form of F-6-P (78.7). The accumulation of $^{13}$C label in C-2 of F-6-P (but no intermediates subsequent to F-6-P in the conventional glycolytic pathway) shows that glucose is being metabolised via glucose-6-phosphate ('G-6-P') as far as F-6-P, but no further. In other words, this proves that the metabolic block created at the phosphofructokinase stage of glycolysis by the pfk1-1 and pfk2::LEU2 mutations has not been breached by any conceivable mechanism ('leaking', reversion of the pfk1-1 mutation, or suppression of either mutation). The presence of $^{13}$C label in C-3 of F-6-P is also highly significant. This can only have arisen by the conversion of glucose into G-6-P thence via enzymes of the hexose monophosphate pathway including the action of both transketolase and transaldolase to give F-6-P labelled at C-3. Once again, it should be stressed that no known metabolite or product of the conventional glycolytic pathway was observed with $^{13}$C label in any position that would have been derived from F-6-P labelled at C-3. Hence, the $^{13}$C NMR analysis showed that the conventional glycolytic pathway was not used for the metabolism of glucose in this yeast strain.

References

Sanger et al (1982) J. Mol. Biol. 162:729

Narbad et al (1988) Microbios 54:171–179

Sturvinton et al (1984) Mol. Gen. Genet. 194:322–329

Hadfield et al (1987) Gene 52:59–70

Clark and Carbon (1976) Cell 9:91–99

Yanisch-Perron et al (1985) Gene 33:103–119

Maniatis et al (1982) Molecular Cloning, Cold Spring Harbor Laboratory, New York Langridge et al (1980) Anal. Biochem. 103:264–271

Praekelt et al (1994) Yeast 10:481–490

Hanahan (1983) J. Mol. Biol 166:157

Bethesda Research Laboratories (1986) Bethesda Res. Lab. Focus 8(2):9

Dickinson et al (1988) J. Gen. Microbiol. 134:333–337

Dickinson et al (1991) J. Gen. Microbiol. 137:1033–1037

Dickinson et al (1995) Microbiology 141:385–391

Thomson et al (1979) J. Bact. 137(1):502–506

TABLE 1

| | Enzyme Expression in *E. coli* | | | | | | | |
|---|---|---|---|---|---|---|---|---|
| | Gluconate Grown Cells | | | | Glucose Grown Cells | | | |
| Enzyme | JM109 | pGem | Clone 1 | Clone 2 | JM109 | pGem | Clone 1 | Clone 2 |
| ED pathway | 40.55 | 69.82 | 62.05 | 57.30 | 7.69 | 0.00 | 99.03 | 68.39 |
| GND | 93.85 | 226.23 | 218.95 | 89.85 | 261.88 | 201.54 | 164.64 | 176.57 |
| ZWF | 132.12 | 181.24 | 171.30 | 145.38 | 429.84 | 326.30 | 323.30 | 324.76 |
| Isocit DH | 132.71 | 658.73 | 722.34 | 245.84 | 481.20 | 233.69 | 492.18 | 299.02 |

Specific activity = nmoles/min/mg protein
Key:
ED = Entner Doudoroff
GND = 6-phosphogluconate dehydrogenase
ZWF = Glucose 6-phosphate dehydrogenase
Isocit DH = Isocitrate dehydrogenase

TABLE 2

Analysis of Fermentation Samples

| Strain | Time (days) | Ethanol (% w/v) | Residual Glucose (% w/v) | Yeast Crop Increase (g) |
|---|---|---|---|---|
| 37.1.6 | 13 | 0.01 | 9.12 | — |
| DFY70 | 13 | 0.01 | 9.50 | — |
| H54-2B (wild-type) | 13 | 1.13 | 8.08 | — |
| 37.1.6/pWB44 | 13 | 3.87 | 4.06 | — |
| 37.1.6/pWB44 | 20 | 5.56 | 1.42 | 2.89 |

TABLE 3

Analysis of Fermentation Samples

| Strain | Time (days) | Ethanol (% w/v) | Residual Sugars (mono- & disaccharides) (% w/v) | Yeast crop Increase (g) |
|---|---|---|---|---|
| 37.1.6/pWB44 | 30 | 3.08 | 3.71 | 3.92 |
| 37.1.6/pWB44 | 30 | 3.28 | 3.77 | 4.19 |

TABLE 4

Ethanol Yield/Growth Comparisons

| Yeast Strain | Ratio of Yeast Growth (gm/100 ml culture) to Ethanol Produced (v/v) |
|---|---|
| A1 | 0.47 |
| A1/3 | 0.50 |
| A1/1 | 0.59 |
| A1/66 | 0.49 |
| A2 | 0.47 |
| A3 | 0.53 |
| A4 | 0.59 |
| 37.1.6/pWB44 Expt 1 | 0.20 |
| 37.1.6/pWB44 Expt 2 | 0.20 |

---

We claim:

1. A transformed yeast that expresses the enzymes phosphogluconate dehydratase and 2-keto-3-deoxygluconate 6-phosphate aldolase; whereby, in fermentation, a sugar is converted to pyruvate via the Entner-Doudoroff pathway.

2. The transformed yeast according to claim 1, which additionally expresses an alcohol dehydrogenase which can utilize NADPH as a co-factor.

3. The transformed yeast according to claim 1 or claim 2, which doesnot express an enzyme among those by which glucose-6-phosphate is converted to pyruvate via the Embden-Meyerhof pathway.

4. The transformed yeast according to claim 3, wherein the non-expressed enzyme is phosphofructokinase.

5. The transformed yeast according to claim 1 or 2, wherein either or both of the Entner-Doudoroff and Embden-Meyerhof pathways can be switched on or off.

6. The transformed yeast according to claim 1 or 2, in immobilized form.

7. The transformed yeast according to claim 1 or 2, of the genus Saccharomyces.

8. A recombinant DNA molecule that encodes the enzymes phosphogluconate dehydratase and 2-keto-3-deoxygluconate-6-phosphate aldolase, wherein at least one of the genes encoding said enzymes is operably linked to a genetic sequence that promotes transcription and/or translation in yeast.

9. A recombinant DNA molecule according to claim 8, further comprise a sequence which transcribes an anti-sense message for a non-expressed enzyme wherein said non-expressed enzyme is an enzyme among those by which glucose-6-phosphate is converted to pyruvate via the Embden-Meyerhof pathway.

10. A recombinant DNA molecule DNA according to claim 8 or claim 9, additionally encoding an alcohol dehydrogenase which can utilize NADPH as a co-factor.

11. A method of converting sugar to alcohol, comprising fermenting in the presence of a transformed yeast that expresses the enzymes phosphogluconate dehydratase and 2-keto-3-deoxygluconate 6-phosphate aldolase; whereby, in fermentation, a sugar is converted to pyruvate via the Entner-Doudoroff pathway.

12. The method according to claim 11, wherein said fermenting produces fuel alcohol.

13. A method for brewing cider or distilling wine, comprising fermenting in the presence of a transformed yeast that expresses the enzymes phosphogluconate dehydratase and 2-keto-3-deoxygluconate 6-phosphate aldolase; whereby, in fermentation, a sugar is converted to pyruvate via the Entner-Doudoroff pathway.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="oligonucleotide"

( x i ) SEQUENCE DESCRIPTION: SEQ ID NO:1:

TAATCAGGCG AGAGAAAACT CTGATGAA        28

( 2 ) INFORMATION FOR SEQ ID NO:2:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="oligonucleotide"

( x i ) SEQUENCE DESCRIPTION: SEQ ID NO:2:

TAATCAGGCG AGAGAATTCT AAAATGAA        28

( 2 ) INFORMATION FOR SEQ ID NO:3:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="oligonucleotide"

( x i ) SEQUENCE DESCRIPTION: SEQ ID NO:3:

TCGCATCGGG CATTTTGACT TTTACAGC                                      28

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="oligonucleotide"

( x i ) SEQUENCE DESCRIPTION: SEQ ID NO:4:

TCGCATCGGG AATTCTGACT TTTACAG                                       27

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="oligonucleotide"

( x i ) SEQUENCE DESCRIPTION: SEQ ID NO:5:

GACAACTCAA TTTCAGGAGC CTTTATGAAT                                 30

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="oligonucleotide"

( x i ) SEQUENCE DESCRIPTION: SEQ ID NO:6:

GACAACTCGA ATTCAGGATC CAAAATGAAT                                 30

( 2 ) INFORMATION FOR SEQ ID NO:7:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="oligonucleotide"

( x i ) SEQUENCE DESCRIPTION: SEQ ID NO:7:

CCTGATTACA AATTTGTCGT CTTAAAAGT                                   29

( 2 ) INFORMATION FOR SEQ ID NO:8:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="oligonucleotide"

( x i ) SEQUENCE DESCRIPTION: SEQ ID NO:8:

CCTGAATTCA AATTTGTCGT CTTAAAAGT        29

( 2 ) INFORMATION FOR SEQ ID NO:9:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="oligonucleotide"

( x i ) SEQUENCE DESCRIPTION: SEQ ID NO:9:

TGAAAAATTC TGCTGTTTAA ACTTAAGTCC        30

( 2 ) INFORMATION FOR SEQ ID NO:10:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="oligonucleotide"

( x i ) SEQUENCE DESCRIPTION: SEQ ID NO:10:

CGACATTTTC AGTCTTAAGG GCTACGCT        28

( 2 ) INFORMATION FOR SEQ ID NO:11:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="oligonucleotide"

( x i ) SEQUENCE DESCRIPTION: SEQ ID NO:11:

GAATTCCCGG GGATCGGTCG ACCTGCAGCC AAGCTT        36

( 2 ) INFORMATION FOR SEQ ID NO:12:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="oligonucleotide"

( x i ) SEQUENCE DESCRIPTION: SEQ ID NO:12:

GAATTCCCGG GGATCCGTCG ACCTGCAGCC AAGCTT        36